US008445702B2

(12) United States Patent
Gee

(10) Patent No.: US 8,445,702 B2
(45) Date of Patent: May 21, 2013

(54) ZINC BINDING COMPOUNDS AND THEIR METHOD OF USE

(75) Inventor: Kyle Gee, Springfiled, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/030,743

(22) Filed: Feb. 18, 2011

(65) Prior Publication Data

US 2011/0159517 A1 Jun. 30, 2011

Related U.S. Application Data

(63) Continuation of application No. 12/167,210, filed on Jul. 2, 2008, now abandoned, which is a continuation of application No. 10/840,712, filed on May 5, 2004, now abandoned.

(51) Int. Cl.
*C07D 311/88* (2006.01)
*G01N 33/20* (2006.01)

(52) U.S. Cl.
USPC .............................. 549/225; 436/84

(58) Field of Classification Search
USPC .............................. 549/225; 436/84
See application file for complete search history.

(56) References Cited

U.S. PATENT DOCUMENTS

| | | | |
|---|---|---|---|
| 4,384,042 A | 5/1983 | Miike et al. |
| 4,520,110 A | 5/1985 | Stryer et al. |
| 4,542,104 A | 9/1985 | Stryer et al. |
| 4,603,209 A | 7/1986 | Tsien et al. |
| 4,774,339 A | 9/1988 | Haugland et al. |
| 4,810,636 A | 3/1989 | Corey et al. |
| 4,812,409 A | 3/1989 | Babb et al. |
| 4,849,362 A | 7/1989 | Demarinis et al. |
| 4,859,582 A | 8/1989 | Stryer et al. |
| 4,945,171 A | 7/1990 | Haugland et al. |
| 5,049,673 A | 9/1991 | Tsien et al. |
| 5,055,556 A | 10/1991 | Stryer et al. |
| 5,187,288 A | 2/1993 | Kang et al. |
| 5,196,306 A | 3/1993 | Bobrow et al. |
| 5,208,148 A | 5/1993 | Haugland et al. |
| 5,227,487 A | 7/1993 | Haugland et al. |
| 5,242,805 A | 9/1993 | Naleway et al. |
| 5,248,782 A | 9/1993 | Haugland et al. |
| 5,268,486 A | 12/1993 | Waggoner et al. |
| 5,274,113 A | 12/1993 | Kang et al. |
| 5,316,906 A | 5/1994 | Haugland et al. |
| 5,362,628 A | 11/1994 | Haugland et al. |
| 5,433,896 A | 7/1995 | Kang et al. |
| 5,442,045 A | 8/1995 | Haugland et al. |
| 5,443,986 A | 8/1995 | Haughland et al. |
| 5,451,343 A | 9/1995 | Neckers et al. |
| 5,453,517 A | 9/1995 | Kuhn et al. |
| 5,459,268 A | 10/1995 | Haugland et al. |
| 5,459,276 A | 10/1995 | Kuhn et al. |
| 5,486,616 A | 1/1996 | Waggoner et al. |
| 5,501,980 A | 3/1996 | Katerinopoulos et al. |
| 5,516,911 A | 5/1996 | London et al. |
| 5,569,587 A | 10/1996 | Waggoner |
| 5,569,766 A | 10/1996 | Waggoner et al. |
| 5,576,424 A | 11/1996 | Mao et al. |
| 5,583,001 A | 12/1996 | Bobrow et al. |
| 5,627,027 A | 5/1997 | Waggoner |
| 5,656,554 A | 8/1997 | Desai et al. |
| 5,686,261 A | 11/1997 | Zhang et al. |
| 5,696,157 A | 12/1997 | Wang et al. |
| 5,731,158 A | 3/1998 | Bobrow et al. |
| 5,773,227 A | 6/1998 | Kuhn et al. |
| 5,773,236 A | 6/1998 | Diwu et al. |
| 5,798,276 A | 8/1998 | Haugland et al. |
| 5,800,996 A | 9/1998 | Lee et al. |
| 5,830,912 A | 11/1998 | Gee et al. |
| 5,846,737 A | 12/1998 | Kang |
| 5,863,727 A | 1/1999 | Lee et al. |
| 5,945,526 A | 8/1999 | Lee et al. |
| 6,008,373 A | 12/1999 | Waggoner et al. |
| 6,008,379 A | 12/1999 | Benson et al. |
| 6,048,982 A | 4/2000 | Waggoner et al. |
| 6,130,101 A | 10/2000 | Mao et al. |
| 6,140,494 A | 10/2000 | Hamilton et al. |
| 6,162,931 A | 12/2000 | Gee et al. |
| 6,184,379 B1 | 2/2001 | Josel et al. |
| 6,221,606 B1 | 4/2001 | Benson et al. |
| 6,229,055 B1 | 5/2001 | Klaubert et al. |
| 6,335,440 B1 | 1/2002 | Lee et al. |
| 6,339,392 B1 | 1/2002 | Ashihara et al. |
| 6,348,599 B1 | 2/2002 | Cummins et al. |
| 6,358,684 B1 | 3/2002 | Lee |

(Continued)

OTHER PUBLICATIONS

Sensi et al., Cell Calcium (2003), 34(3), 281-284.*
U.S. Appl. No. 09/557,275, filed Dec. 16, 2003.
U.S. Appl. No. 09/922,333, filed Apr. 6, 2004.
U.S. Appl. No. 09/969,853, filed Dec. 13, 2005.
U.S. Appl. No. 09/968,401, filed Dec. 20, 2005.
Berg, Jeremy M. et al., "The galvanization of biology: a growing appreciation for the roles of zinc", *Science*, vol. 271, No. 4141, Feb. 23, 1996, 1081-1085.
Brown, Abraham M. et al., "Zn2+ inhibits alpha-ketoglutarate-stimulated mitochondrial respiration and the isolated alpha-ketogultarate dehydrogenase complex", *The Journal of Biological Chemistry*, vol. 275, No. 18, May 5, 2000, 13441-13447.

(Continued)

*Primary Examiner* — Nizal Chandrakumar
(74) *Attorney, Agent, or Firm* — Life Technologies Corporation

(57) ABSTRACT

The present invention provides a metal chelator and methods that facilitate binding, detecting, monitoring and quantitating of zinc ions in a sample. The metal chelating moiety of the zinc-binding compound is an analog of the well-known calcium chelator, BAPTA (1,2-bis(2-aminophenoxy)ethane-N, N,N',N'-tetraacetic acid), wherein the chelating moiety has been modified from a tetraacetic acid moiety to a tri- di- or monoacetic moiety. This change in acetic acid groups on the metal chelating moiety results in the selective bindings of zinc ions in the presence of calcium ions, both of which are present in biological fluids and intracellular cytosolic fluid and organelles.

10 Claims, 3 Drawing Sheets

U.S. PATENT DOCUMENTS

| | | | |
|---|---|---|---|
| 6,372,445 | B1 | 4/2002 | Davis et al. |
| 6,403,807 | B1 | 6/2002 | Singh et al. |
| 2002/0039793 | A1 | 4/2002 | Colvin |
| 2003/0162298 | A1 | 8/2003 | Nagano et al. |

OTHER PUBLICATIONS

Buckman, Jennifer F. et al., "Mito Tracker labeling in primary neuronal and astrocytic cultures: influence of mitochondrial membrane potential and oxidants", *Journal of Neuroscience Methods*, vol. 104, No. 2, 2001, 165-176.

Budde, T. et al., "Imaging free zinc in synaptic terminals in live hippocampal slices", *Neuroscience*, vol. 79, No. 2, 1997, 347-358.

Burdette, Shawn C. et al., ""Fluorescent sensors for Zn(2+) based on a fluorescein platform: synthesis, properties and intracellular distribution"", *J Am Chem Soc*, vol. 123, No. 32, 2001, 7831-7841.

Collins, Tony J. et al., "Mitochondria are morphologically and functionally heterogeneous within cells", *The EMBO Journal*, vol. 21, No. 7, 2002, 1616-1627.

Fahrni, Christoph J. et al., "Aqueous Coordination Chemistry of Quinoline-Based Fluorescence Probes for the Biological Chemistry of Zinc", *J. Am. Chem. Soc.*, vol. 121, 1999, 11448-11458.

Frederickson, Christopher J. et al., "A quinoline fluorescence method for visualizing and assaying the histochemically reactive zinc (bouton zinc) in the brain", *Journal of Neuroscience Methods*, vol. 20, No. 2, 1987, 91-103.

Frederickson, Christopher J. et al., "Importance of Zinc in the Central Nervous System: The Zinc-Containing Neuron", *American Society for Nutrional Sciences*, 2000, 1471S-14783S.

Frederickson, Christopher J., "Neurobiology of Zinc and Zinc-Containing Neurons", *International Review of Neurobiology*, vol. 31, 1989, 145-239.

Gee, Kyle R. et al., "Measuring zinc in living cells. A new generation of sensitive and selective fluorescent probes", *Cell Calcium*, vol. 31, No. 5, 2002, 245-251.

Gee, Kyle R. et al., "Detection and Imaging of Zinc Secretion from Pancreatic Beta-Cells Using a New Fluorescent Zinc Indicator", *Journal of the American Chemical Society*, vol. 124, No. 5, 2002, 776-778.

Grynkiewicz, Grzegorz et al., "A new generation of Ca++ indicators with greatly improved fluorescent properties", *The Journal of Biological Chemistry*, vol. 260, No. 6, 1985, 3440-3450.

Haugland, Richard P., "Molecular Probes Handbook of Fluorescent Probes and Research Products", *9th Edition, 2002 (CD-Rom Format)*, Molecular Probes, 2002.

Hirano, Tomoya et al., "Improvement and biological applications of fluorescent probes for zinc, ZnAFs", *J Am Chem Soc*, vol. 124, No. 33, 2002, 6555-6562.

Hirano, Tomoya et al., "Novel Zinc Fluorescent Probes Excitable with Visible Light for Biological Applications We Thank Prof. E. Kimura and Prof. T. Koike for advice on the chemistry of macrocyclic polyamines", *Angewandte Chemie International Edition in English*, vol. 39, No. 6, 2000, 1052-1054.

Jiang, Dongmei et al., "Zn (2+) induces permeability transition pore opening and release of pro-apoptotic peptides from neuronal mitochondria", *The Journal of Biological Chemistry*, vol. 276, No. 50, Dec. 14, 2001, 47524-47529.

Kirschke, Catherine P. et al., "ZnT7, a novel mammalian zinc transporter, accumulates zinc in the Golgi apparatus", *The Journal of Biological Chemistry*, vol. 278, No. 6, Feb. 7, 2003, 4096-4102.

Kleiner, D., "The effect of Zn2+ ions on mitochondrial electron transport", *Archives of Biochemistry and Biophysics*, vol. 165, No. 1, 1974, 121-125.

Link, Thomas A. et al., "Zinc ions inhibit the QP center of bovine heart mitochondrial bc1 complex by blocking a protonable group", *The Journal of Biological Chemistry*, vol. 270, No. 42, Oct. 20, 1995, 25001-25006.

Manev, Hari et al., ""Characterization of Zinc-induced neuronal death in primary cultures of rat cerebellar granule cells"", *Experimental Neurology*, vol. 146, No. 1, Article# EN976510, 1997, 171-178

Maruyama, S. et al., "A novel, cell-permeable, fluorescent probe for ratiometric imaging of zinc ion", *J Am Chem Soc*, vol. 124, No. 36, 2002, 10650-1.

Minta, Akwasi et al., "Flourescent indicators for cytosolic calcium based on rhodamine and fluorescein chromophores", *The Journal of Biological Chemistry*, vol. 264, No. 14, May 15, 1989, 8171-8178.

Outten, Caryn E. et al., "Femtomolar sensitivity of metalloregulatory proteins controlling Zinc homeostasis", *Science*, vol. 292, No. 5526, Jun. 29, 2001, 2488-2492.

Sensi, Stefano H. et al., ""AMPA/kainate receptor-triggered Zn2+ entry into cortical neurons induces mitochondrial Zn2+ uptake and persistent mitochondrial dysfunction"", *European Journal of Neuroscience*, vol. 12, No. 10, 2000, 3813-3818.

Sensi, Stefano L. et al., "Preferential Zn2+ influx through Ca2+-permeable AMPA/kainate channels triggers prolonged mitochondrial superoxide production", *Proceedings of the National Academy of Sciences (PNAS)*, vol. 96, No. 5, Mar. 1999, 2414-2419.

Sensi, Stefano L. et al., "Mitochondrial sequestration and Ca(2+)-dependent release of cytosolic Zn(2+) loads in cortical neurons", *Neurobiology of Disease*, vol. 12, No. 2, 2002, 100-108.

Skulachev, V. P. et al., "Inhibition of the respiratory chain by zinc ions", *Biochemical and Biophysical Research Communications*, vol. 26, No. 1, 1967, 1-6.

Snitsarev, Vladislav et al., "Fluorescent detection of Zn (2+)-rich vesicles with Zinquin: mechanism of action in lipid environments", *Biophysical Journal*, vol. 80, No. 3, Mar. 2001, 1538-46.

Tsien, R. Y. et al., "A non-disruptive technique for loading calcium buffers and indicators into cells", *Nature*, vol. 290, No. 5806, Apr. 1981, 527-8.

Weiss, John H., "Zn (2+): a novel ionic mediator of neural injury in brain disease", *Trends Pharmacol Sci*, vol. 21, No. 10, 2000, 395-401.

Wudarczyk, Jolanta et al., "Zinc as an inducer of the membrane permeability transition in rat liver mitochondria", *Archives of Biochemistry and Biophysics*, vol. 363, No. 1, Mar. 1, 1999, 1-8.

Yin, Hong Z. et al., "Zn(2+) permeates Ca(2+) permeable AMPA/Kainate channels and triggers selective neural injury", *Neuroreport*, vol. 6, No. 18, 1995, 2553-6.

* cited by examiner

ZINC BINDING COMPOUNDS AND THEIR METHOD OF USE

CROSS-REFERENCE TO RELATED APPLICATIONS

This application is a continuation of U.S. Ser. No. 12/167,210, filed Jul. 2, 2008 (now abandoned), which is a continuation of U.S. Ser. No. 10/840,712, filed May 5, 2004 (now abandoned), the disclosures of which are herein incorporated by reference.

FIELD OF THE INVENTION

The present invention relates to novel compositions and methods for the detection of physiological concentrations of zinc ions. The invention has applications in the fields of cell biology, neurology, nutrition, immunology, reproductive biology, cancer and proteomics.

BACKGROUND OF THE INVENTION

Identification and quantification of low levels of zinc ions is important for biological research, diagnosis of metal ion induced disease state, accurate quantification in foodstuff and environmental samples. The zinc(II) ion ($Zn^{2+}$) plays an important role in biology and nutrition and when present in high concentrations in the environment can have a toxic effect on biological systems (Berg, J M, et al. *Science* (1996) 271: 1081-5).

$Zn^{2+}$ is known to play an important role in protein structure, gene regulation, protein synthesis, intracellular protein trafficking, hormone function and immune function and is considered an essential element wherein the USDA recommends daily consumption of a small amount of $Zn^{2+}$ (Kirschke C P, et al., J Biol Chem (2003) 278(6): 4096-4102). Recently $Zn^{2+}$ has emerged as an important player in neurotransmission (Frederickson, C J. *Int Rev Neurobiol* (1989) 31: 145-238) and neural injury (Frederickson C J, et al. *J Nutr.* (2000) 130:1471-83; Weiss J H, et al. *Trends Pharm Sci.* (2000) 21:395-400). Much of the total biological zinc is tightly bound to proteins and enzymes (Outten C E, et al. *Science* (2001) 292:2488-92). Rapid rises in intracellular free $Zn^{2+}$ ($[Zn^{2+}]_i$) have been linked to neuronal injury in transient global ischemia and epilepsy (Frederickson, C J. *Int Rev Neurobiol*; Weiss J H, et al. *Trends Pharm Sci.* (supra)). The mechanisms by which $Zn^{2+}$ exerts potent neurotoxic effects are still largely unknown. It has been suggested that among the intracellular targets of $Zn^{2+}$ dependent neurotoxicity, $Zn^{2+}$ sequestration into mitochondria may play a critical role (Manev H, et al. *Exp Neurol* (1997) 146:171-8; Sensi S L, et al., *PNAS* (1999) 96:2414-9; Sensi S L, et al. *Eur J Neurosci* (2000) 12:3813-8). As with $Ca^{2+}$, upon excessive cytosolic $Zn^{2+}$ loading, mitochondria take up $Zn^{2+}$ and help to restore intracellular $Zn^{2+}$ homeostasis (Sensi S L, et al. *Eur J Neurosci*, supra). However, once in the mitochondria, $Zn^{2+}$ can trigger a prolonged disruption of the functioning of these organelles. Indeed, $Zn^{2+}$ has been shown to have potent effects on mitochondria (Skulachev V P, et al. Biochem Biophys Res Commun (1967) 26:1-6; Kleiner D. Arch Biochem Biophys (1974) 165:121-5; Link T A, et al. J Biol Chem (1995) 270:25001-6; Wudarczyk J, et al. Arch Biochem Biophys (1999) 363:1-8; Brown A M, et al. J Biol Chem (2000) 275:13441-7; Jiang D, et al. J Biol Chem (2001) 276: 47524-9). For instance, in neuronal mitochondria, rises in $[Zn^{2+}]_m$ promote loss of mitochondrial membrane potential ($\Delta\Psi_m$) and generation of reactive oxygen species (ROS) as well as release of pro-apoptotic factors (Sensi S L, et al. Neurobiol Dis (2002) 10:100-108).

Due to the low concentration of physiological free $Zn^{2+}$ (nanomolar), elucidation of the biology of zinc has been hampered by a lack of suitable detection and imaging reagents. Thus, at least for biological research there is need for more sensitive indicators than have previously been available. Indicators that have been previously used include fluorescent sulfonamides of 8-aminoquinolines (Fahrni C J, et al JACS (1999) 121:11448; Snitsarev V. et al., Biophys J. (2001) 80:1538; Budde T, Neuroscience (1997) 79:347; Frederickson C J., et al. (1987) 20:91. These indicators are UV excitable, potentially damaging, and exhibit low signal levels. Alternatively, visible light indicators have been developed that demonstrate a higher affinity for $Zn^{2+}$ and a brighter signal than the 8-aminoquinolines based indicators (Burdette S C, eta I., JACS (2001) 123(32):7831-41; Hirano T, et al., Angew Chem Int Ed Engl (2000) 39(6):1052-1054; Maruyama S. et al., JACS (2002) 124(36):10650-1; Hirano T, et al., JACS (2002) 124(23):6555-62). However, at least some of these visible light indicators are only useful in a limited pH range and tend to localize in intracellular acidic compartments. This is due to the chelator moieties of the indicator that become significantly protonated at physiological pH.

Therefore, there is a need for zinc-binding compounds that selectively bind zinc ions in the presence of other physiological relevant metal ions, have a high affinity for physiological concentrations of zinc ions (nanomolar concentrations), can be effectively utilized at a physiological pH and are environmentally sensitive to zinc ions, i.e. show a significant change in signal after being bound by zinc ions.

Herein we disclose novel zinc-binding compounds that selectively bind zinc ions in the presence of physiological concentrations of calcium. These zinc-binding compounds provide powerful tools for selectively binding zinc ions in intracellular compartments, biological fluids and environmental samples. These compounds overcome the limitations of known zinc indicators. Specifically, zinc-binding compounds are disclosed that localize to the mitochondrial membrane and selectively bind zinc ions.

SUMMARY OF THE INVENTION

The present invention provides zinc-binding compounds and methods for the selective binding and detection of physiological concentrations of zinc ions. The zinc-binding compounds find utility in binding (sequestering), detecting (monitoring and/or quantitating) free zinc ions. Detection also includes the screening of drug candidates that affect intracellular zinc ion concentrations, ion channels and zinc-binding proteins). The zinc ions include intracellular zinc, zinc that has been secreted by cells wherein the zinc is in an assay buffer or a biological fluid, zinc ions added exogenously to an assay system or zinc ions sequestered by a protein.

The metal chelating moiety of the zinc-binding compound is an analog of the well-known calcium chelator, BAPTA (1,2-bis(2-aminophenoxy)ethane-N,N,N',N'-tetraacetic acid), wherein the chelating moiety has been modified from a tetraacetic acid moiety to a triacetic, diacetic or monoacetic acid moiety. This change in acetic acid groups on the metal chelating moiety unexpectedly results in the selective binding of zinc ions in the presence of calcium ions, both of which are present in biological fluids and intracellular cytosolic fluid and organelles. Due to the relatively high concentration of physiological intracellular calcium compared to zinc and the fact that BAPTA binds calcium with higher affinity than zinc, BAPTA is an ineffective chelator for binding physiological zinc ions in the presence of calcium ions. However, we found that by lowering the affinity for calcium that triacetic acid analog of BAPTA chelating moieties preferentially bind zinc in the presence of calcium ions at physiological concentrations of both ions.

Therefore, the present compounds have the general formula:

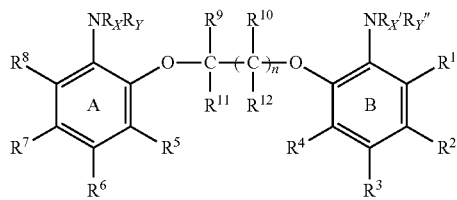

wherein $R_X$, $R_Y$, $R_X'$ and $R_Y''$ is hydrogen, $C_1$-$C_6$ alkyl or —$CH_2CO_2R$, wherein R is H, a salt ion or $CH_2OC(O)CH_3$ with the proviso that at least one of $R_X$, $R_Y$, $R_X'$ or $R_Y''$ is hydrogen or said alkyl;

wherein $R^1$, $R^2$, $R^3$, $R^4$, $R^5$, $R^6$, $R^7$ and $R^8$ are independently selected from the group consisting of hydrogen, halogen, $C_1$ to $C_6$ alkyl ($CH_2$), methoxy (—$OCH_3$), hydroxyl (—OH), $C_2$-$C_6$ alkoxy (—$OCH_2$), alicyclic, heteroalicyclic, aryl, heteroaryl, amino (—NR'R"), aldehyde, carboxyl, azido, nitro, nitroso, cyano, thioether, sulfinyl, reactive group, solid support, carrier molecule and reporter molecule; or two adjacent $R^1$, $R^2$, $R^3$, $R^4$, $R^5$, $R^6$, $R^7$ and $R^8$ substitutents form a fused reporter group;

wherein R' and R" are independently selected from the group consisting of H, $C_1$-$C_6$ alkyl, substituted alkyl, $C_1$-$C_6$ carboxyalkyl (—$CH_2COOH$), an alpha-acyloxyalkyl, a biologically compatible salt, aryl, substituted aryl, aryl alkyl, substituted aryl alkyl, heteroaryl, and substituted heteroaryl;

$R^9$, $R^{10}$, $R^{11}$ and $R^{12}$ are independently selected from the group consisting of hydrogen, lower alkyl, reactive group, carrier molecule, solid support and reactive molecule, or adjacent substituents $R^9$ and $R^{10}$ or $R^{11}$ and $R^{12}$ in combination constitute a 5-membered or 6-membered alicyclic or heterocyclic ring, and with the proviso that when said $R^3$ or $R^6$ is attached to a reporter molecule by a single covalent bond the reporter molecule is not 2,7 difluoro-3-hydroxyxanthen-6-one.

In an exemplary embodiment exactly one of said $R_X$, $R_Y$, $R_X'$ or $R_Y''$ is hydrogen or $C_1$-$C_6$ alkyl to form a triacetic acid analog of BAPTA, which has a higher affinity for zinc ions than the di- or monoacetic analogs. In a preferred embodiment exactly one of said $R_X$, $R_Y$, $R_X'$ or $R_Y''$ is hydrogen and the remaining $R_X$, $R_Y$, $R_X'$ or $R_Y'$ are —$CH_2CO_2R$ wherein R is H, a salt ion or $CH_2OC(O)CH_3$. In one aspect R is H or a salt ion to form a cell impermeant zinc-binding compound. In another aspect R is $CH_2OC(O)CH_3$ to form a cell permeant analog that freely enters live cells and is converted to the cell impermeant version by non-specific esterases to provide for a compound that is well retained in the cell and that has affinity for intracellular zinc ions. Thus, in a further aspect of the invention, for either the cell permeant or cell impermeant version, at least one of $R^1$-$R^8$ is a reporter molecule to form a zinc ion indicator of the present invention.

The reporter molecule can be any molecule that produces a detectable signal, directly or indirectly, selected from the group consisting of a dye (chromophore or fluorophore), fluorescent protein, phosphorescent dye and a tandem dye. Typically the reporter molecule is a dye wherein the zinc-binding compounds comprising a dye demonstrate a change in the detectable signal when zinc ions are bound by the zinc-binding compounds of the present invention. Most preferred are dyes that are xanthene, cyanine, benzofuran, quinazolinone, indole, benzazole, borapolyazaindacene, dansyl, pyrene, naphthalene, coumarin, oxazine, benzofuran, quinazolinone, and derivatives thereof. Typically the dye is a xanthene selected from the group consisting of fluorescein or derivative thereof, rhodamine or derivative thereof, rhodol or derivative thereof or rosamine or a derivative thereof. For zinc-binding compounds that are mitochondrian selective, cationic fluorescent xanthylium dye derivatives, including 3-aminoxanthene-6-imine and any dye disclosed in U.S. Pat. No. 5,459,268, are particularly useful.

The reporter molecules of the present invention are independently substituted by substituents selected from the group consisting of hydrogen, halogen, amino, substituted amino, alkyl, substituted alkyl, aryl, substituted aryl, heteroaryl, substituted heteroaryl, alkoxy, sulfo, reactive group and carrier molecule.

In an exemplary embodiment, at least one of $R^1$-$R^8$ is a, reactive group, solid support, carrier molecule wherein these compounds find use in binding and detecting zinc ions. The reactive group finds use in conjugating the present compounds to a carrier molecule or solid support, which may facilitate binding of zinc ions including selectively localizing the zinc-binding compounds or be used to sequester zinc ions from a solution. Carrier molecules may also amplify a signal such as when an enzyme and enzyme substrate are present.

The reactive groups of the present compound are selected from the group consisting of an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a halotriazine, a hydrazine, an imido ester, an isocyanate, an isothiocyanate, a maleimide, a phosphoramidite, a reactive platinum complex, a silyl halide, a sulfonyl halide, a thiol and a photoactivatable group. Typically the reactive group is a carboxylic acid, succinimidyl ester of a carboxylic acid, hydrazide, amine or a maleimide, which are useful for conjugating to proteins such as antibodies.

The carrier molecules are selected from the group consisting of an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell or a virus. Typically the carrier molecule is selected from the group consisting of an antibody or fragment thereof, an avidin or streptavidin, a biotin, a dextran, an IgG binding protein, a fluorescent protein, agarose, and a non-biological microparticle.

The solid supports of the present invention are selected from the group consisting of solid support is selected from the group consisting of a microfluidic chip, a silicon chip, a microscope slide, a microplate well, silica gels, polymeric membranes, particles, derivatized plastic films, glass beads, cotton, plastic beads, alumina gels, polysaccharides, polyvinylchloride, polypropylene, polyethylene, nylon, latex bead, magnetic bead, paramagnetic bead, and superparamagnetic bead. In one aspect the solid supports are Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose or starch.

The carrier molecule, reactive group, solid support and optionally the reporter molecule further comprise a linker that covalently attaches the substituent to the present compound. The linker is a single covalent bond, or a covalent linkage that is linear or branched, cyclic or heterocyclic, saturated or unsaturated, having 1-20 nonhydrogen atoms selected from the group consisting of C, N, P, O and S; and are composed of any combination of ether, thioether, amine, ester, carboxamide, sulfonamide, hydrazide bonds and aromatic or heteroaromatic bonds.

In one embodiment, reporter molecules that comprise a linker include, but are not limited to fluorescent proteins, phosphorescent dyes, tandem dyes, xanthenes (fluorescein or derivative thereof, rhodamine or derivative thereof, rhodol or derivative thereof or rosamine or a derivative thereof), cyanines, quinazolinones, indoles, borapolyazaindacenes, dansyls, pyrenes, naphthalenes, coumarins, oxazines, quinazolinones, and derivatives thereof.

Alternatively, some reporter molecules may share ring A or ring B (atoms) of the present compounds to form a fused reporter molecule wherein no linker is present. Thus, at least two adjacent $R^1$, $R^2$, $R^3$, $R^4$, $R^5$, $R^6$, $R^7$ and $R^8$ substituents form a fused reporter group. In one aspect these reporter molecules include, but are not limited to benzofuran and benzazole It is appreciated that the present invention encompasses a wide range of compounds that find utility in binding and optionally detecting zinc ions. The choice of reporter molecule and other substituents on the acetic acid analogs of BAPTA chelating moiety result in zinc-binding compounds with different spectral properties, affinity for zinc ions and live cell properties. We found that the new Compounds 4 and 5 wherein the reporter molecule is a 3-aminoxanthene-6-imine dye that is attached by a single covalent bond to the metal chelating moiety of the present invention exemplify a particularly useful combination. Compound 5, after being converted to Compound 4 in live cells, effectively binds and detects nanomolar concentrations of zinc ions and co-localizes to the mitochondrial membrane in live cells with a mitochondrian selective stain (MitoTracker Green FM). Thus, this particular zinc-binding compound provides a very powerful tool for the monitoring of zinc ions associated with mitochondrial metabolism (Kleiner D., Archives of Biochemistry and Biophysics (1974) 165: 121-125; Sensi S, et al., Neurobiology of Disease (2002) 10:100-108; Sensi S, et al. European J. of Neuroscience (2000) 12:3813-3818) and drugs that specifically modulate zinc ions associated with mitochondrial metabolism.

In another embodiment, the present compounds form a complex with a target metal ion, wherein the metal ion is selected from the group consisting of $Zn^{2+}$, $Fe^{2+}$ and $Ca^{2+}$. Typically the metal ion is Zn2+. In another aspect, the complex further comprises a protein that has affinity for the target metal ions wherein a ternary complex is formed.

Thus, the methods of the present invention comprise contacting a sample with a present compound wherein zinc ions are bound. When detection is desired the present compounds further comprise a reporter molecule wherein the sample is illuminated by an appropriate wavelength and the zinc ions are detected.

It is understood that the present invention does not cover the zinc indicator sold under the trade name FluoZin-3 (Molecular Probes, Inc.) wherein the reporter molecule, 2,7 difluoro-3-hydroxyxanthen-6-one, is attached by a single bond to the triacetic acid chelating moiety of the present invention at the corresponding $R^6$ position.

DETAILED DESCRIPTION OF THE INVENTION

Introduction

Figure 1:
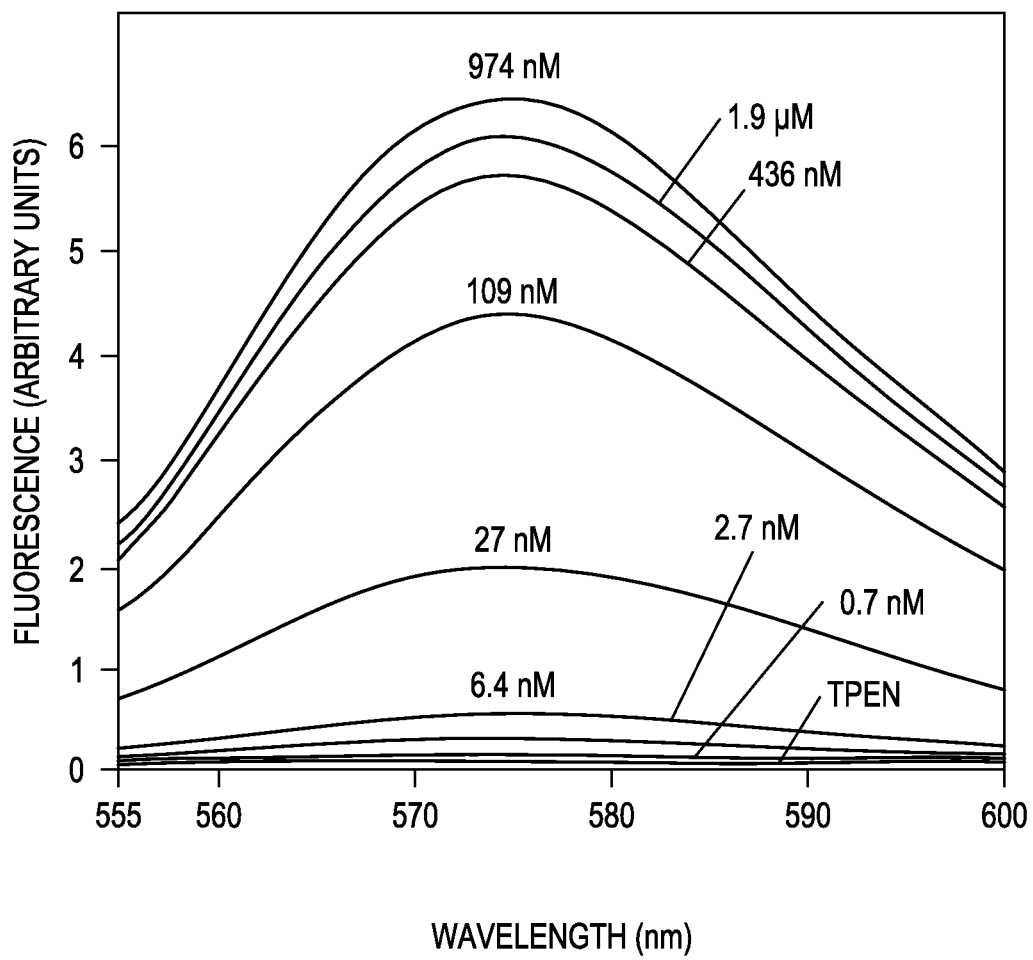
FIG. 1: Shows the spectroscopic response of Compound 4 to increasing concentrations of buffered zinc chloride at pH 7.0 (50 mM MOPS, 100 mM KCl). Zero $Zn^{2+}$ measurements were made in the presence of the zinc chelator TPEN. Excitation was at 545 nm. See, Example 2.

The present invention provides zinc-binding compounds for the binding, including sequestering of ions, detection, monitoring and quantification of zinc ions, including physiological concentrations of zinc ions that are present in intracellular and extracellular biological fluids. The zinc-binding compounds preferentially bind zinc ions in the presence of physiological concentrations of calcium ions, this property being a function of the chelating moiety of the zinc-binding compounds, and provides a mechanism for binding and detecting zinc ions in the presence of calcium ions.

The zinc-binding compounds of the present invention are typically represented by the general formula A(B) wherein A is a reporter molecule, reactive group or carrier molecule and B is a triacetic, diacetic or monoacetic acid analog of BAPTA, herein referred to as "acetic acid analog of BAPTA". The reactive group and carrier molecule and optionally the reporter molecule are attached to the chelating moiety by a linker, wherein the linker is a single covalent bond or a series of stable covalent bonds. In this instance, the zinc-binding compounds typically have the general formula $A(L)_m(B)$ wherein m is 0-4.

Definitions

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a present compound" includes a plurality of compounds and reference to "a zinc ion" includes a plurality of ions and the like.

Unless defined otherwise, all technical and scientific terms used herein have the same meaning as commonly understood by one of ordinary skill in the art to which this invention is related. The following terms are defined for purposes of the invention as described herein.

The term "affinity" as used herein refers to the strength of the binding interaction of two molecules, such as a metal chelating compound and a metal ion or a positively charged moiety and a negatively charged moiety.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL's ENCYCLOPEDIA OF PRACTICAL ORGANIC CHEMISTRY $5^{TH}$ ED., Longman Scientific and Technical Ltd., Essex, 1991, pp. 809-816; and Heller, *Acc. Chem. Res.* 23: 128 (1990).

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "acyl" or "alkanoyl" by itself or in combination with another term, means, unless otherwise stated, a stable straight or branched chain, or cyclic hydrocarbon radical, or combinations thereof, consisting of the stated number of carbon atoms and an acyl radical on at least one terminus of the alkane radical. The "acyl radical" is the group derived from a carboxylic acid by removing the —OH moiety therefrom.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

Exemplary alkyl groups of use in the present invention contain between about one and about twenty-five carbon atoms (e.g. methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a straight or branched chain, or cyclic carbon-containing radical, or combinations thereof, consisting of the stated number of carbon atoms and at least one heteroatom selected from the group consisting of O, N, Si, P and S, and wherein the nitrogen, phosphorous and sulfur atoms are optionally oxidized, and the nitrogen heteroatom is optionally be quaternized. The heteroatom(s) O, N, P, S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic moiety that can be a single ring or multiple rings (preferably from 1 to 3 rings), which are fused together or linked covalently.

The term "heteroaryl" as used herein refers to an aryl group as defined above in which one or more carbon atoms have been replaced by a non-carbon atom, especially nitrogen, oxygen, or sulfur. For example, but not as a limitation, such groups include furyl, tetrahydrofuryl, pyrrolyl, pyrrolidinyl, thienyl, tetrahydrothienyl, oxazolyl, isoxazolyl, triazolyl, thiazolyl, isothiazolyl, pyrazolyl, pyrazolidinyl, oxadiazolyl, thiadiazolyl, imidazolyl, imidazolinyl, pyridyl, pyridaziyl, triazinyl, piperidinyl, morpholinyl, thiomorpholinyl, pyrazinyl, piperainyl, pyrimidinyl, naphthyridinyl, benzofuranyl, benzothienyl, indolyl, indolinyl, indolizinyl, indazolyl, quinolizinyl, qunolinyl, isoquinolinyl, cinnolinyl, phthalazinyl, quinazolinyl, quinoxalinyl, pteridinyl, quinuclidinyl, carbazolyl, acridinyl, phenazinyl, phenothizinyl, phenoxazinyl, purinyl, benzimidazolyl and benzthiazolyl and their aromatic ring-fused analogs. Many fluorophores are comprised of heteroaryl groups and include, without limitations, xanthenes, oxazines, benzazolium derivatives (including cyanines and carbocyanines), borapolyazaindacenes, benzofurans, indoles and quinazolones.

The above heterocyclic groups may further include one or more substituents at one or more carbon and/or non-carbon atoms of the heteroaryl group, e.g., alkyl; aryl; heterocycle; halogen; nitro; cyano; hydroxyl, alkoxyl or aryloxyl; thio or mercapto, alkyl- or arylthio; amino, alkyl-, aryl-, dialkyl-, diaryl-, or arylalkylamino; aminocarbonyl, alkylaminocarbonyl, arylaminocarbonyl, dialkylaminocarbonyl, diarylaminocarbonyl or arylalkylaminocarbonyl; carboxyl, or alkyl- or aryloxycarbonyl; aldehyde; aryl- or alkylcarbonyl; iminyl, or aryl- or alkyliminyl; sulfo; alkyl- or arylsulfonyl; hydroximinyl, or aryl- or alkoximinyl. In addition, two or more alkyl substituents may be combined to form fused heterocycle-alkyl ring systems. Substituents including heterocyclic groups (e.g., heteroaryloxy, and heteroaralkylthio) are defined by analogy to the above-described terms.

The term "heterocycloalkyl" as used herein refers to a heterocycle group that is joined to a parent structure by one or more alkyl groups as described above, e.g., 2-piperidylmethyl, and the like. The term "heterocycloalkyl" refers to a heteroaryl group that is joined to a parent structure by one or more alkyl groups as described above, e.g., 2-thienylmethyl, and the like.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR'", —NR—C(NR'R")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR'", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—.

The substituents R, R', R" and R'" are preferably independently selected from hydrogen or substituted or unsubstituted $(C_1-C_6)$alkyl.

As used herein, the term "heteroatom" includes oxygen (O), nitrogen (N), sulfur (S), phosphorus (P) and silicon (Si).

The term "amino" or "amine group" refers to the group —NR'R" (or NRR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —NRR'R" and its biologically compatible anionic counterions.

The term "aqueous solution" as used herein refers to a solution that is predominantly water and retains the solution characteristics of water. Where the aqueous solution contains solvents in addition to water, water is typically the predominant solvent.

The term "biotin" as used herein refers to any biotin derivative, including without limitation, substituted and unsubstituted biotin, and analogs and derivatives thereof, as well as substituted and unsubstituted derivatives of caproylamidobiotin, biocytin, desthiobiotin, desthiobiocytin, iminobiotin, and biotin sulfone.

The term "biotin-binding protein" as used herein refers to any protein that binds selectively to biotin, including without limitation, antibodies to biotin, substituted or unsubstituted avidin, and analogs and derivatives thereof, as well as substituted and unsubstituted derivatives of antibodies, streptavidin, ferritin avidin, nitroavidin, nitrostreptavidin, Neutravidin™ avidin (a de-glycosylated modified avidin having an isoelectric point near neutral) and their dye-, enzyme-, or polymer-modified variants and immobilized forms of the biotin-binding proteins.

The term "buffer" as used herein refers to a system that acts to minimize the change in acidity or basicity of the solution against addition or depletion of chemical substances.

The term "carbonyl" as used herein refers to the functional group —(C=O)—. However, it will be appreciated that this group may be replaced with other well-known groups that have similar electronic and/or steric character, such as thiocarbonyl (—(C=S)—); sulfinyl (—S(O)—); sulfonyl (—SO$_2$)—), phosphonyl (—PO$_2$—).

The term "carboxy" or "carboxyl" refers to the group —R'(COOR) where R' is alkyl, substituted alkyl, aryl, substituted aryl, arylalkyl, substituted arylalkyl, heteroaryl, or substituted heteroaryl. R is hydrogen, a salt or —CH$_2$OC(O)CH$_3$.

The term "carrier molecule" as used herein refers to a compound of the present invention that is covalently bonded to a biological or a non-biological component. Such components include, but are not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof.

The term "complex" as used herein refers to the association of two or more molecules, usually by non-covalent bonding.

The term "detectable response" as used herein refers to a change in or an occurrence of, a signal that is directly or indirectly detectable either by observation or by instrumentation.

Typically, the detectable response is an optical response resulting in a change in the wavelength distribution patterns or intensity of absorbance or fluorescence or a change in light scatter, fluorescence lifetime, fluorescence polarization, or a combination of the above parameters. Alternatively, the detectable response is an occurrence of a signal wherein the fluorophore is inherently fluorescent and does not produce a change in signal upon binding to a metal ion. Alternatively, the detectable response is the result of a signal, such as color, fluorescence, radioactivity or another physical property of the detectable label becoming spatially localized in a subset of a sample such as in a gel, on a blot, or an array, in a well of a micoplate, in a microfluidic chamber, or on a microparticle as the result of formation of a ternary complex of the invention that comprises a zinc binding protein.

The term "directly detectable" as used herein refers to the presence of a detectable label or the signal generated from a detectable label that is immediately detectable by observation, instrumentation, or film without requiring chemical modifications or additional substances. For example, a fluorophore produces a directly detectable response.

The term "dye" as used herein refers to a compound that emits light to produce an observable detectable signal. "Dye" includes fluorescent and nonfluorescent compounds that include without limitations pigments, fluorophores, chemiluminescent compounds, luminescent compounds and chromophores. The term "fluorophore" as used herein refers to a compound that is inherently fluorescent or demonstrates a change in fluorescence upon binding to a biological compound or metal ion, i.e., fluorogenic. Numerous fluorophores are known to those skilled in the art and include, but are not limited to, coumarin, acridine, furan, indole, quinoline, cyanine, benzofuran, quinazolinone, benzazole, borapolyazaindacene and xanthenes, with the latter including fluoroscein, rhodamine, rhodol, rosamine and derivatives thereof as well as other fluorophores described in RICHARD P. HAUGLAND, MOLECULAR PROBES HANDBOOK OF FLUORESCENT PROBES AND RESEARCH CHEMICALS ($9^{th}$ edition, CD-ROM, 2002).

The term "enzyme" as used herein refers to a protein molecule produced by living organisms, or through chemical modification of a natural protein molecule, that catalyzes a chemical reaction of other substances without itself being destroyed or altered upon completion of the reactions. Examples of other substances, include, but are not limited to chemiluminescent, chromogenic and fluorogenic substances or protein-based substrates.

The term "free zinc" as used herein refers to zinc ions that are available to be chelated. Alternatively, "sequestered zinc" refers to zinc ions that are bound be a competing ligand such as a zinc-binding protein.

The term "kit" as used herein refers to a packaged set of related components, typically one or more compounds or compositions.

The term "Linker" or "L", as used herein, refers to a single covalent bond or a series of stable covalent bonds incorporating 1-30 nonhydrogen atoms selected from the group consisting of C, N, O, S and P that covalently attach the phosphate-binding compounds to another moiety such as a chemically reactive group or a phosphorylated target molecule. Exemplary linking members include a moiety that includes —C(O)NH—, —C(O)O—, —NH—, —S—, —O—, and the like. A "cleavable linker" is a linker that has one or more cleavable groups that may be broken by the result of a reaction or condition. The term "cleavable group" refers to a moiety that allows for release of a portion, e.g., a reporter molecule, carrier molecule or solid support, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleaveable groups are known in the art. See, for example, Jung et al., *Biochem. Biophys. Acta,* 761: 152-162 (1983); Joshi et al., *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989). Moreover a broad range of cleavable, bifunctional (both homo- and hetero-bifunctional) spacer arms are commercially available.

An exemplary cleavable group, an ester, is cleavable group that may be cleaved by a reagent, e.g. sodium hydroxide, resulting in a carboxylate-containing fragment and a hydroxyl-containing product.

The linker can be used to attach the compound to another component of a conjugate, such as a targeting moiety (e.g., antibody, ligand, non-covalent protein-binding group, etc.), an analyte, a biomolecule, a drug and the like.

The term "metal chelator" or "metal chelating moiety" as used herein refers to a chemical compound that combines with a metal ion to form a chelate ring structure. For the purposes of the present invention the metal chelator is an acetic acid (tri-, di- or mono-) analog of BAPTA that has demonstrated affinity for $Zn^{2+}$, $Ca^{2+}$ and $Fe^{2+}$. These ions may be free in solution or they may be sequestered by a metal ion-binding compound, such as a zinc binding protein. The metal chelators are optionally substituted by substituents that adjust the ion-binding affinity, solubility, chemical reactivity, spectral properties or other physical properties of the compound.

The term "metal ion" as used herein refers to any physiological, environmental and or nutritional relevant metal ion. Such metal ions may also have affinity for proteins and include, but are not limited to $Zn^{2+}$, $Fe^{2+}$ and $Ca^{2+}$.

The terms "protein" and "polypeptide" are used herein in a generic sense to include polymers of amino acid residues of any length. The term "peptide" is used herein to refer to polypeptides having less than 250 amino acid residues, typically less than 100 amino acid residues, more typically less than 15 amino acid residues. The terms apply to amino acid polymers in which one or more amino acid residues are an artificial chemical analogue of a corresponding naturally occurring amino acid, as well as to naturally occurring amino acid polymers. The peptide or protein may be further conjugated to or complexed with other moieties such as dyes, haptens, radioactive isotopes, natural and synthetic polymers (including microspheres), glass, metals and metallic particles, proteins and nucleic acids.

The term "reactive group" as used herein refers to a group that is capable of reacting with another chemical group to form a covalent bond, i.e. is covalently reactive under suitable reaction conditions, and generally represents a point of attachment for another substance. The reactive group is a moiety, such as a photoactivatable group, carboxylic acid or succinimidyl ester, on the compounds of the present invention that is capable of chemically reacting with a functional group on a different compound to form a covalent linkage resulting in a phosphate-binding labeled component. Reactive groups generally include nucleophiles, electrophiles and photoactivatable groups.

Exemplary reactive groups include, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

The term "reporter molecule" as used herein refers to a detectable moiety that is used to facilitate detection of zinc ions and zinc-binding proteins in combination with the metal-chelating moiety of the present invention, acetic acid analog of BAPTA. Illustrative reporter molecules include molecules that can be directly observed or measured or indirectly observed or measured such as fluorophores, radioactive and enzyme reporter molecules (Patton, W., et al, *J. Chromatography B: Biomedical Applications* (2002) 771:3-31; Patton, W., et al, *Electrophoresis* (2000) 21:1123-1144). Such reporter molecules include, but are not limited to, radiolabels that can be measured with radiation-counting devices; pigments, dyes (fluorophore or chromophore) or other chromogens that can be visually observed or measured with a spectrophotometer; tandem dyes that participate in energy transfer, spin labels that can be measured with a spin label analyzer; and fluorescent proteins or fluorophores, where the output signal is generated by the excitation of a suitable molecular adduct and that can be visualized by excitation with light that is absorbed by the dye or can be measured with standard fluorometers or imaging systems, for example or metal particles, e.g. gold or silver particles or metallic bar codes that can be detected by their optical or light-scattering properties. The reporter molecule can be a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term reporter molecule can also refer to a "tag", hapten or other ligand that can bind selectively to a labeled molecule such that the labeled molecule, when added subsequently, is used to generate a detectable signal. For example, one can use biotin as a tag and then use an avidin or streptavidin conjugate of horseradish peroxidase (HRP) to bind to the tag, and then use a chromogenic substrate (e.g., tetramethylbenzidine) or a fluorogenic substrate such as Amplex® Red reagent (Molecular Probes, Inc.) to detect the presence of HRP. Numerous reporter molecules and tags and methods for their selective detection are known by those of skill in the art and include, but are not limited to, particles, fluorophores, haptens, enzymes and their chromogenic, fluorogenic and chemiluminescent substrates and other labels that are described in the MOLECULAR PROBES HANDBOOK, supra. In addition, present reporter molecules can be substituted with substituents that alter the ion-binding affinity of the present compound, solubility, chemical reactivity, spectral properties or other physical properties of the reporter molecule.

The term "sample" as used herein refers to any material that may contain metal ions, as defined above. Typically, the sample is a live cell or a biological fluid that comprises endogenous host cell proteins or foodstuff or an environmental sample such as a water sample. The sample may be in an aqueous solution, a viable cell culture or immobilized on a solid or semi solid surface such as a polyacrylamide gel, membrane blot or on a microarray.

The term "ternary complex" as used herein refers to a composition that simultaneously comprises a present metal ion chelating compound, a metal ion of the present invention and a metal ion binding molecule such as a zinc binding protein, wherein the metal ions simultaneously have affinity for both the metal-chelating moiety of the present compound and the metal ion binding molecule, and wherein the metal ion forms a bridge between the two molecules. Unless limited by the context of their use, the terms "binding" and "complex formation" in this invention mean the process of formation of this ternary complex or the formation of a complex consisting essentially of the present compound and a present metal ion.

The term "zinc-binding compound" or "present compound" as used herein refers to the metal chelating moiety that is the triacetic, diacetic or monoacetic acid analog of BAPTA. For ease of describing the present invention, these compounds are collectively referred to as "acetic acid analogs of BAPTA", thus it is understood that these references, unless dictated by context, includes the tri- di- and monoacetic acid analogs.

These compounds are typically substituted by substituents that modify ion affinity, chemical reactivity, spectral properties and solubility. Typically, the acetic acid analog of BAPTA is substituted by a reporter molecule, reactive group, solid support or carrier molecule that facilitate binding, detection, isolation, sequestration, and monitoring of the present metal ions. Preferably, the present compounds are substituted by reporter molecules that facilitate detection and monitoring of the metal ions. Thus, the zinc-binding compounds of the present invention typically have the general formula A(B) wherein A is a reporter molecule, reactive group or carrier molecule, B is a metal chelating moiety. The reporter molecule may share atoms of the chelating moiety, be attached by a single covalent bond or attached by a linker comprising multiple stable bonds. Reactive groups and carrier molecules are attached by a single covalent bond or by a linker comprising multiple stable bonds. Thus, when these substituents are attached by a single covalent bond or a series of stable bonds the zinc binding compound has the general formula A(L)m(B) wherein L is a Linker that covalently attaches the substituents to the metal chelating moiety and m is 0-4. For purposes of the invention it is understood that while the present compounds are typically referred to as zinc-binding compounds this is not intended to be limiting to only zinc ions as the present compounds have a demonstrated ability to bind other metal ions such as $Ca^{2+}$ and $Fe^{2+}$. The metal ions, such as zinc ions can be free in solutions or non-covalently bound to another molecule such as a protein.

The Compounds

In general, for ease of understanding the present invention, the zinc-binding compounds and corresponding substituents will first be described in detail, followed by the many and varied methods in which the zinc-binding compounds and metal ions find uses, which is followed by exemplified methods of use and synthesis of certain novel compounds that are particularly advantageous for use with the methods of the present invention.

1. Acetic Acid Analogs of BAPTA

The metal chelating moiety of the present invention is a derivative of the well know calcium chelating moiety 1,2-bis (2-aminophenoxy)ethane-N,N,N',N'-tetraacetic acid (BAPTA). In an effort to devise a zinc probe that is selective for physiological levels of zinc but not calcium ions, which are typically present in much higher concentrations, we unexpectedly found that by removing one, two or three of the acetic acid groups from the BAPTA compound that the new compound could selectively detect physiological levels of zinc ions. The modification to the BAPTA chelating moiety reduced the affinity for calcium ions by approximately 100-1000× fold but not the affinity for zinc ions resulting in a chelator that preferentially binds zinc ions in the presence of physiological concentrations of calcium ions. This metal chelating moiety is a tri- di- or monoacetic acid analog of BAPTA and has the following formula:

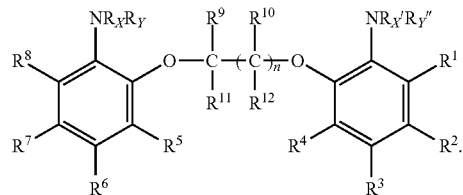

$R_X$, $R_Y$, $R_{X'}$ and $R_{Y'}$ are independently hydrogen (H), acetic acid or an acetic acid group that has been substituted by an acetyloxy methyl (AM) ester wherein acetic acid is represented by $CH_2COOR$ wherein R is H, a salt ion or an AM ester represented by $CH_2OC(O)CH_3$. The novelty of the metal chelating moiety of the present invention is that the moiety is a tri- di- or monoacetic acid compound; therefore, at least one of $R_X$, $R_Y$, $R_{X'}$ and $R_{Y'}$ is H or $C_1$-$C_6$ alkyl and the remaining $R_X$, $R_Y$, $R_{X'}$ and $R_{Y'}$ groups are $CH_2COOR$. In one embodiment, the compound is a triacetic acid analog of BAPTA wherein exactly one of $R_X$, $R_Y$, $R_{X'}$ and $R_{Y'}$ is H or $C_1$-$C_6$ alkyl. Typically, exactly one of $R_X$, $R_Y$, $R_{X'}$ and $R_{Y'}$ is H or methyl, preferably exactly one of $R_X$, $R_Y$, $R_{X'}$ and $R_{Y'}$ hydrogen.

In a further embodiment, modification of carboxylic groups with acetoxymethyl (AM) ester groups results in uncharged molecules than can penetrate cell membranes—live cell versions of the zinc-binding compounds. This includes the carboxylic groups of the acetic acid groups or other carboxylic groups on the metal chelating moiety. In this particular embodiment, typically at least one R is $CH_2OC(O)CH_3$, preferably at least two R and most preferred at least three R are $CH_2OC(O)CH_3$. Once inside the cells, the lipophilic blocking groups are cleaved by nonspecific esterases revealing a metal chelating moiety of the present invention, e.g., a triacetic acid moiety. For example, see Example 3 and 4 wherein Compound 5 is loaded into neurons and converted to Compound 4 for the detection of zinc ions. Alternatively, acetate groups on a compound of the present invention can also allow a compound to enter a live cell.

In another embodiment, R is H or a salt ion and the zinc binding compounds of the present invention are used to bind and detect zinc ions that are not contained by a lipid bilayer. This includes zinc ions that are free in solution such as a biological fluid or zinc that has been released from cells and zinc that is sequestered by proteins. When R is H or a salt ion the compounds are impermeant to cellular membranes.

The acetic acid analog metal chelating moiety comprises two benzene rings that are joined by a $C_1$-$C_3$ hydrocarbon bridge (n is 1, 2 or 3) terminated by oxygen atoms, including methylenedioxy (—$OCH_2O$—), ethylenedioxy (—$OCH_2CH_2O$—) or propylenedioxy (—$OCH_2CH_2CH_2O$—) bridging groups, where each benzene ring is optionally substituted by one or more substituents that adjust the metal ion-binding affinity, solubility, chemical reactivity, spectral properties or other physical properties of the compound. The benzene ring substituents ($R^1$, $R^2$, $R^3$, $R^4$, $R^5$, $R^6$, $R^7$ and $R^8$) and the bridging group substituents ($R^9$, $R^{10}$, $R^{11}$ and $R^{12}$) are typically selected from substituents that are found on BAPTA compounds. This includes any substituents disclosed in U.S. Pat. Nos. 4,603,209; 4,795,712; 4,849,362; 5,049,673; 5,453,517; 5,459,276; 5,516,911; 5,501,980; 6,162,931 and 5,773,227.

In an exemplary embodiment, $R^1$, $R^2$, $R^3$, $R^4$, $R^5$, $R^6$, $R^7$ and $R^8$ are independently selected from the group consisting of hydrogen, halogen, $C_1$-$C_6$ alkyl ($CH_2$), methoxy (—$OCH_3$), hydroxyl (—OH), $C_2$-$C_6$ alkoxy (—$OCH_2$), alicyclic, heteroalicyclic, aryl, heteroaryl, amino (—NR'R"), aldehyde, carboxyl, azido, nitro, nitroso, cyano, thioether, sulfinyl, carrier molecule, solid support, reactive group and reporter molecule. The amino substituents, R' and R", are independently selected from the group consisting of H, $C_1$-$C_6$ alkyl, substituted alkyl, $C_1$-$C_6$ carboxyalkyl, an alpha-acyloxyalkyl, a biologically compatible salt, aryl, substituted aryl, aryl alkyl, substituted aryl alkyl, heteroaryl, and substituted heteroaryl. Each alkyl portion is optionally substituted by halogen, amino, hydroxy, or amino.

In addition, any two adjacent substituents $R^1$-$R^8$, taken in combination, form a fused six-membered benzo moiety or a reporter molecule, each of which is optionally and independently substituted by halogen, azido, nitro, nitroso, amino, cyano, $C_1$-$C_6$ alkyl or $C_1$-$C_6$ alkoxy. Each alkyl portion is optionally substituted by halogen, amino, hydroxy, or amino.

In one embodiment, at least one of $R^1$, $R^2$, $R^3$, $R^4$, $R^5$, $R^6$, $R^7$ and $R^8$ is a carrier molecule, solid support, reactive group and reporter molecule. Typically, at least one of $R^3$ or $R^6$ is a carrier molecule, solid support, reactive group or reporter molecule.

The bridging group substituents, $R^9$, $R^{10}$, $R^{11}$, and $R^{12}$, are typically independently selected from the group consisting of hydrogen, lower alkyl, carrier molecule, solid support, reactive group and reporter molecule or adjacent substituents $R^9$ and $R^{10}$ or $R^{11}$ and $R^{12}$ in combination constitute a 5-membered or 6-membered alicyclic or heterocyclic ring.

In a preferred embodiment exactly one of said $R_X$, $R_Y$, $R_X'$ or $R_Y''$ is hydrogen or $C_1$-$C_6$ alkyl. Most preferred for binding zinc ions at least one of $R_X$, $R_Y$, $R_X'$ or $R_Y''$ is hydrogen. In a further embodiment, the remaining $R_X$, $R_Y$, $R_X'$ or $R_Y''$ are —$CH_2CO_2R$ wherein R is H, a salt ion or $CH_2OC(O)CH_3$. In one embodiment R is R is H or a salt ion to form a cell impermeant zinc-binding compound. In another embodiment R is $CH_2OC(O)CH_3$ to form a cell permeant zinc-binding compound.

In one embodiment, the present compounds further comprise a reporter group to form a zinc indicator compound. These compounds are particularly useful for detecting zinc ions. In one aspect the present compounds comprise exactly one reporter group. In another embodiment, the present compounds further comprise a carrier molecule. In yet another embodiment, the present compounds further comprise a solid support. In another embodiment, the present compounds further comprise a solid support and a reporter group, which are particularly useful for high content screening.

2 Optional Substituents of the Acetic Acid Analogs of BAPTA
a) Linkers

The reactive group, carrier molecules, solid support and optionally the reporter molecule comprise a linker (L) that is used to covalently attach the substituents to the acetic acid analogs of BAPTA. When a linker is present the zinc-binding compounds are represented by the formula A(L)(B) wherein L is a linker that is a single covalent bond or a series of stable bonds. Thus, the reporter molecule, solid support, carrier molecule or reactive group may be directly attached (where Linker is a single bond) to the metal chelating moiety or attached through a series of stable bonds. When the linker is a series of stable covalent bonds the linker typically incorporates 1-30 nonhydrogen atoms selected from the group consisting of C, N, O, S and P. When the linker is not a single covalent bond, the linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. Typically the linker incorporates less than 15 nonhydrogen atoms and are composed of any combination of ether, thioether, thiourea, amine, ester, carboxamide, sulfonamide, hydrazide bonds and aromatic or heteroaromatic bonds. Typically the linker is a combination of single carbon-carbon bonds and carboxamide, sulfonamide or thioether bonds. The bonds of the Linker typically result in the following moieties that can be found in the Linker: ether, thioether, carboxamide, thiourea, sulfonamide, urea, urethane, hydrazine, alkyl, aryl, heteroaryl, alkoky, cycloalkyl and amine moieties. Examples of a linker include substituted or unsubstituted polymethylene, arylene, alkylarylene, arylenealkyl, or arylthio.

In one embodiment, L contains 1-6 carbon atoms; in another, L comprises a thioether linkage. In another embodiment, L is or incorporates the formula —$(CH_2)_d(CONH(CH_2)_e)_z$— or —$O(CH_2)_d(CONH(CH_2)_e)_z$—, where d is an integer from 0-5, e is an integer from 1-5 and z is 0 or 1. In a further embodiment, L is or incorporates the formula —O—$(CH_2)$—. In yet another embodiment, L is or incorporates a phenylene or a 2-carboxy-substituted phenylene.

Any combination of linkers may be used to attach the reporter molecule, carrier molecule, solid support or reactive group and the metal chelating moiety together, typically a chelating moiety will have one or two linkers attached that may be the same or different. The linker may also be substituted to alter the physical properties of the fluorescent zinc-binding compound, such as binding affinity of the chelating moiety and spectral properties of the dye.

Another important feature of the linker is to provide an adequate space between the reporter molecule and the metal chelating moiety so as to prevent the reporter molecule from providing a steric hinderance to the binding of the zinc ion for the chelating moiety of the zinc-binding compound. Therefore, the linker of the present zinc-binding compounds is important for (1) attaching the reporter molecule to the metal chelating moiety, (2) providing an adequate space between the reporter molecule and the metal chelating moiety so as not to sterically hinder the affinity of the chelating moiety and the zinc ions and (3) for altering the affinity of the chelating moiety for the zinc ions either by the choice of the atoms of the linker or indirectly by addition of substituents to the linker.

However, it is important to understand that a linker is not an essential component of the zinc-binding compounds.

Depending on the reporter molecule, a linker may not be necessary wherein the reporter molecule shares atoms with the metal chelating moiety. A reporter molecule that exemplifies this is the dye benzofuran wherein one of the benzene rings of the dye is also one of the benzene rings of the metal chelating moiety. The well know calcium indicator, Fura-2, is one such compound wherein a modification from a tetraacetic acid to a triacetic acid compound results in a zinc-binding compound of the present invention (Compound 13). This compound is particularly useful for performing ratiometric analysis of zinc ions.

b) Reactive Groups

In another exemplary embodiment of the invention, the compounds of the invention are chemically reactive, and are substituted by at least one reactive group. The reactive group functions as the site of attachment for another moiety, such as a reporter molecule, a carrier molecule or a solid support, wherein the reactive group chemically reacts with an appropriate reactive or functional group on the reporter molecule, carrier molecule or solid support. Thus, in another aspect of the present invention the compounds comprise an acetic acid analog of BAPTA, a reactive group moiety and optionally a carrier molecule and/or a solid support.

In an exemplary embodiment, the compounds of the invention further comprise a reactive group which is a member selected from an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a halotriazine, a hydrazine, an imido ester, an isocyanate, an isothiocyanate, a maleimide, a phosphoramidite, a photoactivatable group, a reactive platinum complex, a silyl halide, a sulfonyl halide, and a thiol. In a particular embodiment the reactive group is selected from the group consisting of carboxylic acid, succinimidyl ester of a carboxylic acid, hydrazide, amine and a maleimide. In exemplary embodiment, at least one member selected from $R^1$, $R^2$, $R^3$, $R^4$, $R^5$, $R^6$, $R^7$, $R^8$, $R^9$, $R^{10}$, $R^{11}$, and $R^{12}$ is a reactive group. Preferably, at least one of $R^1$, $R^2$, $R^3$, $R^4$, $R^5$, $R^6$, $R^7$, and $R^8$ is a reactive group, most preferred is at least one of $R^3$ or $R^6$. Alternatively, if the present compound comprises a reporter group, carrier molecule or solid support a reactive group may be covalently attached independently to those substituents, allowing for further conjugation to a reporter molecule, carrier molecule or solid support.

These reactive groups are synthesized during the formation of the chelating moiety and reporter molecule, carrier molecule and solid support containing compounds to provide acetic acid analogs of BAPTA and reactive group-containing compounds. In this way, compounds incorporating a reactive group can be covalently attached to a wide variety of carrier molecules, reporter molecules or solid supports that contain or are modified to contain functional groups with suitable reactivity, resulting in chemical attachment of the components. In an exemplary embodiment, the reactive group of the compounds of the invention and the functional group of the carrier molecule, reporter molecule or solid support comprise electrophiles and nucleophiles that can generate a covalent linkage between them. Alternatively, the reactive group comprises a photoactivatable group, which becomes chemically reactive only after illumination with light of an appropriate wavelength. Typically, the conjugation reaction between the reactive group and the carrier molecule or solid support or reporter molecule results in one or more atoms of the reactive group being incorporated into a new linkage attaching the acetic acid analogs of BAPTA compound of the invention to the carrier molecule or reporter molecule or solid support.

Selected examples of functional groups and linkages are shown in Table 1, where the reaction of an electrophilic group and a nucleophilic group yields a covalent linkage.

TABLE 1

Examples of some routes to useful covalent linkages

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g., succinimidyloxy (—OC$_4$H$_4$O$_2$) sulfosuccinimidyloxy (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).
**Acyl azides can also rearrange to isocyanates Choice of the reactive group used to attach the compound of the invention to the substance to be conjugated typically depends on the reactive or functional group on the substance to be conjugated and the type or length of covalent linkage desired. The types of functional groups typically present on the organic or inorganic substances (biomolecule or non-biomolecule) include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. A single type of reactive site may be available on the substance (typical for polysaccharides or silica), or a variety of sites may occur (e.g., amines, thiols, alcohols, phenols), as is typical for proteins.

Typically, the reactive group will react with an amine, an alcohol, an aldehyde, a ketone, or with silica. Preferably, reactive groups react with an amine or a thiol functional group, or with silica. In one embodiment, the reactive group is an acrylamide, an activated ester of a carboxylic acid, an acyl azide, an acyl nitrile, an aldehyde, an alkyl halide, a silyl halide, an anhydride, an aniline, an aryl halide, an azide, an aziridine, a boronate, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is particularly meant chemically reactive platinum complexes such as described in U.S. Pat. No. 5,714,327.

Where the reactive group is an activated ester of a carboxylic acid, such as a succinimidyl ester of a carboxylic acid, the resulting compound is particularly useful for preparing conjugates of carrier molecules such as proteins, nucleotides, oligonucleotides, or haptens. Where the reactive group is a maleimide or haloacetamide the resulting compound is particularly useful for conjugation to thiol-containing substances. Where the reactive group is a hydrazide, the resulting compound is particularly useful for conjugation to periodate-oxidized carbohydrates and glycoproteins, and in addition is an aldehyde-fixable polar tracer for cell microinjection. Where the reactive group is a silyl halide, the resulting compound is particularly useful for conjugation to silica surfaces, particularly where the silica surface is incorporated into a fiber optic probe subsequently used for remote ion detection or quantitation.

In a particular aspect, the reactive group is a photoactivatable group such that the group is only converted to a reactive species after illumination with an appropriate wavelength. An appropriate wavelength is generally a UV wavelength that is less than 400 nm. This method provides for specific attachment to only the target molecules, either in solution or immobilized on a solid or semi-solid matrix. Photoactivatable reactive groups include, without limitation, benzophenones, aryl azides and diazirines.

Preferably, the reactive group is a photoactivatable group, succinimidyl ester of a carboxylic acid, a haloacetamide, a hydrazine, an isothiocyanate, a maleimide group, an aliphatic amine, a silyl halide, a cadaverine or a psoralen. More preferably, the reactive group is a succinimidyl ester of a carboxylic acid, a maleimide, an iodoacetamide, or a silyl halide. In a particular embodiment the reactive group is a succinimidyl ester of a carboxylic acid or an maleimide.

c) Reporter Molecules

The reporter molecules of the present invention confer a detectable signal, directly or indirectly, to the target zinc ions. This results in the ability to detect, monitor and quantitate zinc ions in a sample. When the zinc ions are associated with other ions or proteins, such as zinc binding proteins to form a ternary complex, those associated molecules can be detected and measured.

Thus, in an exemplary embodiment, the present compound is covalently bound to a reporter group, See Compound 4, 5 and 13. The reporter molecule can be attached the compound through the chelating moiety by a linker or share atoms with the chelating moiety wherein no linker is present. If the compound has a reactive group, then the reporter molecule can alternatively be linked to the compound through the reactive group. The reactive group may contain both a reactive functional moiety and a linker, or only the reactive functional moiety.

The present reporter molecules can be any reporter molecule known to one skilled in the art and when the reporter molecule is either covalently linked to a metal-chelating moiety or comprises part of the metal-chelating moiety wherein no linker is present, forms a zinc-binding compound of the present invention that is useful for the detection of zinc ions. Reporter molecules include, without limitation, a dye, (chromophore or fluorophore), a fluorescent protein, a phosphorescent dye, a tandem dye (energy transfer pair), a microparticle, a hapten, an enzyme and a radioisotope. Preferred reporter molecules include dyes, fluorescent proteins, haptens, and enzymes. When the reporter molecule is a chromophore the zinc-binding compounds are chromogenic indicators, or more preferably, the reporter molecule is a fluorophore, resulting in a compound that is a fluorogenic indicator for zinc ions. Therefore, binding a zinc ion to a zinc-binding compound results in a detectable optical response that can be correlated to the presence of zinc ions.

In one embodiment, at least one of $R^1$, $R^2$, $R^3$, $R^4$, $R^5$, $R^6$, $R^7$, $R^8$, $R^9$, $R^{19}$, $R^{11}$ and $R^{12}$ is or is attached to a reporter molecule or any two adjacent $R^1$, $R^2$, $R^3$, $R^4$, $R^5$, $R^6$, $R^7$, and $R^8$ form a fused reporter molecule that share atoms with either ring A or ring B of the acetic acid analog of BAPTA. In a particular aspect at least one of $R^1$, $R^2$, $R^3$, $R^4$, $R^5$, $R^6$, $R^7$, and $R^8$ is or is attached to a reporter molecule. In a preferred aspect, either $R^3$ or $R^6$ is or is attached to a reporter molecule.

Where the detectable response is a fluorescence response, it is typically a change in fluorescence, such as a change in the intensity, excitation or emission wavelength, distribution of fluorescence, fluorescence lifetime, fluorescence polarization, or a combination thereof. Preferably, the detectable optical response upon binding a target zinc ion is a change in fluorescence intensity that is greater than approximately 10-fold relative to the same compound in the absence of zinc, more preferably greater than 50-fold, and most preferably more that 100-fold. This large increase in fluorescent signal over baseline has not been previously observed with other zinc indicators that comprise a different metal chelating moiety. In another aspect, the detectable optical response upon binding the target metal ion is a shift in either the maximal excitation or emission wavelength or both that is greater than about 20 nm, more preferably greater than about 30 nm.

A dye of the present invention is any chemical moiety that exhibits an absorption maximum beyond 280 nm, and when covalently linked to a metal chelating moiety of the present invention, or shares atoms with the metal chelating moiety, forms a zinc-binding compound. A preferred embodiment for detecting zinc ions in live cells or zinc ions secreted from live cells is a fluorogenic zinc-binding compound wherein the reporter molecule is dye. As described above, the covalent linkage can be a single covalent bond or a combination of stable chemical bonds. The covalent linkage binding the dye to the metal chelating moiety is typically a single covalent bond or a substituted alkyl chain that incorporates 1-20 non-hydrogen atoms selected from the group consisting of C, N, O, S and P.

Dyes of the present invention include, without limitation; a pyrene, an anthracene, a naphthalene, an acridine, a stilbene, an indole or benzoindole, an oxazole or benzoxazole, a thiazole or benzothiazole, a 4-amino-7-nitrobenz-2-oxa-1,3-diazole (NBD), a carbocyanine (including any corresponding compounds in U.S. Ser. Nos. 09/557,275; 09/968,401 and 09/969,853 and U.S. Pat. Nos. 6,403,807; 6,348,599; 5,486, 616; 5,268,486; 5,569,587; 5,569,766; 5,627,027 and 6,048, 982), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896), a xanthene (including any corresponding compounds disclosed in U.S. Pat. Nos. 6,162,931; 6,130,101; 6,229,055; 6,339,392; 5,451,343 and U.S. Ser. No. 09/922,333), an oxazine or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459,276; 5,501,980 and 5,830,912), a benzofuran (including an corresponding compounds disclosed in U.S. Pat. Nos. 4,603,209 and 4,849,362) and benzphenalenone (including any corresponding compounds disclosed in U.S. Pat. No. 4,812,409) and derivatives thereof. As used herein, oxazines include resorufins (including any corresponding compounds disclosed in 5,242,805), aminooxazinones, diaminooxazines, and their benzo-substituted analogs.

Where the dye is a xanthene, the dye is optionally a fluorescein, a rhodol (including any corresponding compounds disclosed in U.S. Pat. Nos. 5,227,487 and 5,442,045), a rosamine or a rhodamine (including any corresponding compounds in U.S. Pat. Nos. 5,798,276; 5,846,737; 5,847,162; 6,017,712; 6,025,505; 6,080,852; 6,716,979; 6,562,632). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171).

Preferred dyes of the invention include rhodol, fluorescein, rhodamine, dansyl, benzofuran, indole, cyanine, quinazolinone, pyrene, naphthalene, coumarin, oxazine, benzofuran, indole, a benzazole and borapolyazaindacene. In one embodiment benzofuran and benzazole form a fused reporter molecule with either ring A or ring B of the acetic acid analogs of BAPTA chelating moiety. In another aspect, the reporter molecules xanthene, dansyl, benzofuran, indole, cyanine, quinazolinone, pyrene, naphthalene, coumarin, oxazine, indole, and borapolyazaindacene are independently attached to the chelating moiety by a linker.

Typically the dye contains one or more aromatic or heteroaromatic rings, that are optionally substituted one or more times by a variety of substituents, including without limitation, halogen, nitro, sulfo, cyano, alkyl, perfluoroalkyl, alkoxy, alkenyl, alkynyl, cycloalkyl, arylalkyl, acyl, aryl or heteroaryl ring system, benzo, or other substituents typically present on chromophores or fluorophores known in the art.

In an exemplary embodiment, the dyes are independently substituted by substituents selected from the group consisting of hydrogen, halogen, amino, substituted amino, alkyl, substituted alkyl, aryl, substituted aryl, heteroaryl, substituted heteroaryl, alkoxy, sulfo, reactive group and carrier molecule. In another embodiment, the xanthene dyes of this invention comprise both compounds substituted and unsubstituted on the carbon atom of the central ring of the xanthene by substituents typically found in the xanthene-based dyes such as phenyl and substituted-phenyl moieties. Most preferred dyes are rhodamine, fluorescein, rhodal, rosamine and derivatives thereof. The choice of the dye attached to the chelating moiety will determine the zinc-binding compound's absorption and fluorescence emission properties as well as its live cell properties, i.e. ability to localize to mitochondria.

In an exemplary embodiment, the dye has an absorption maximum beyond 480 nm. In a particularly useful embodiment, the dye absorbs at or near 488 nm to 514 nm (particularly suitable for excitation by the output of the argon-ion laser excitation source) or near 546 nm (particularly suitable for excitation by a mercury arc lamp). As is the case for many dyes, they can also function as both chromophores and fluorophores, resulting in compounds that simultaneously act both as colorimetric and fluorescent labels for zinc ions. Thus, the described fluorescent dyes are also the preferred chromophores of the present invention.

The cationic xanthylium dyes disclosed U.S. Pat. No. 5,459,268 (supra) are useful as a live cell zinc indicator that are mitochondrian selective. We have found that 3-aminoxanthene-6-imine dyes are particularly useful, when comprising a zinc-binding compound of the present invention, for localizing at or near the mitochondrial membrane and binding zinc at that location within the cell. See, example 2.

For zinc-binding compounds that find use in detecting zinc ions wherein a change in detectable signal is not required, i.e. unbound zinc-binding compounds can be washed away and the remaining zinc-binding compounds are bound to zinc ions, the alternative reporter molecules that are haptens, enzymes, fluorescent proteins and tandem dyes (energy transfer dyes) find use as reporter molecules of the present invention. In this aspect, a stable ternary complex is formed between a zinc ion and a zinc-binding molecule (e.g., protein, carrier molecule or solid support). Therefore, these reporter molecules find use wherein the sample is immobilized on a solid or semi-solid matrix or in biological fluids wherein a polarization assay is used to measure zinc ions or alternatively tandem dyes can be used resulting a shift in signal when zinc ions are bound by the zinc-binding compounds.

Enzymes are desirable reporter molecules because amplification of the detectable signal can be obtained, resulting in increased assay sensitivity. The enzyme itself does not produce a detectable response, but functions to break down a substrate when it is contacted by an appropriate substrate such that the converted substrate produces a fluorescent, colorimetric or luminescent signal. Enzymes amplify the detectable signal because one enzyme on a zinc-binding compound can result in multiple substrate molecules being converted to a detectable signal. This is advantageous where there is a low quantity of zinc ions present in the sample or a dye does not exist that will give comparable or stronger signal than the enzyme. Dyes are most preferred because they do not require additional assay steps that can lead to an unstable zinc-binding complex and they do not lend to live cell measurement of zinc ions. The enzyme substrate is selected to yield the preferred measurable product, e.g. color, fluorescence or chemiluminescence. Such substrates are extensively used in the art, many of which are described in the MOLECULAR PROBES HANDBOOK, supra.

A preferred colorimetric or fluorogenic substrate and enzyme combination uses oxidoreductases such as horseradish peroxidase (HRP) and a substrate such as 3,3'-diaminobenzidine (DAB) or 3-amino-9-ethylcarbazole (AEC), which yield a distinguishing color (brown and red, respectively). Other colorimetric oxidoreductase substrates that yield detectable products include, but are not limited to: 2,2-azino-bis(3-ethylbenzothiazoline-6-sulfonic acid) (ABTS), o-phenylenediamine (OPD), 3,3',5,5'-tetramethylbenzidine (TMB), o-dianisidine, 5-aminosalicylic acid and 4-chloro-1-naphthol. Fluorogenic substrates include, but are not limited to, homovanillic acid or 4-hydroxy-3-methoxyphenylacetic acid, reduced phenoxazines and reduced benzothiazines, including Amplex® Red reagent and its variants (U.S. Pat. No. 4,384,042) and reduced dihydroxanthenes, including dihydrofluoresceins (U.S. Pat. No. 6,162,931) and dihydrorhodamines, including dihydrorhodamine 123. Peroxidase substrates that are tyramides (U.S. Pat. Nos. 5,196,306;

5,583,001 and 5,731,158) represent a unique class of peroxidase substrates in that they can be intrinsically detectable before action of the enzyme but are "fixed in place" by the action of a peroxidase in the process described as tyramide signal amplification (TSA). These substrates are extensively utilized to label targets in samples that are cells, tissues or arrays for their subsequent detection by microscopy, flow cytometry, optical scanning and fluorometry.

Another preferred colorimetric (and in some cases fluorogenic) substrate and enzyme combination uses a phosphatase enzyme such as an acid phosphatase or a recombinant version of such a phosphatase in combination with a colorimetric substrate such as 5-bromo-4-chloro-3-indolyl phosphate (BCIP), 6-chloro-3-indolyl phosphate, 5-bromo-6-chloro-3-indolyl phosphate, p-nitrophenyl phosphate, or o-nitrophenyl phosphate or with a fluorogenic substrate such as 4-methylumbelliferyl phosphate, 6,8-difluoro-7-hydroxy-4-methylcoumarinyl phosphate (DiFMUP, U.S. Pat. No. 5,830,912), fluorescein diphosphate, 3-O-methylfluorescein phosphate, resorufin phosphate, 9H-(1,3-dichloro-9,9-dimethylacridin-2-one-7-yl) phosphate (DDAO phosphate), or ELF 97, ELF 39 or related phosphates (U.S. Pat. Nos. 5,316,906 and 5,443,986).

Glycosidases, in particular β-galactosidase, β-glucuronidase and β-glucosidase, are additional suitable enzymes. Appropriate colorimetric substrates include, but are not limited to, 5-bromo-4-chloro-3-indolyl β-D-galactopyranoside (X-gal) and similar indolyl galactosides, glucosides, and glucuronides, o-nitrophenyl β-D-galactopyranoside (ONPG) and p-nitrophenyl β-D-galactopyranoside. Preferred fluorogenic substrates include resoruf in β-D-galactopyranoside, fluorescein digalactoside (FDG), fluorescein diglucuronide and their structural variants (U.S. Pat. Nos. 5,208,148; 5,242,805; 5,362,628; 5,576,424 and 5,773,236), 4-methylumbelliferyl β-D-galactopyranoside, carboxyumbelliferyl β-D-galactopyranoside and fluorinated coumarin β-D-galactopyranosides (U.S. Pat. No. 5,830,912).

Additional enzymes include, but are not limited to, hydrolases such as cholinesterases and peptidases, oxidases such as glucose oxidase and cytochrome oxidases and reductases for which suitable substrates are known.

Enzymes and their appropriate substrates that produce chemiluminescence are preferred for some assays. These include, but are not limited to, natural and recombinant forms of luciferases and aequorins. Chemiluminescence-producing substrates for phosphatases, glycosidases and oxidases such as those containing stable dioxetanes, luminol, isoluminol and acridinium esters are additionally useful. Several chemiluminescent substrates for phosphatase enzymes are known, including the BOLD APB chemiluminescent substrate (Molecular Probes, Inc.).

In addition to enzymes, haptens such as biotin, digoxigenin and 2,4-dinitrophenol are also preferred reporter molecules. Biotin is useful because it can function in an enzyme system to further amplify the detectable signal, and it can function as a tag to be used in affinity chromatography for isolation purposes. For detection purposes, an enzyme conjugate that has affinity for biotin is used, such as avidin-HRP. Subsequently a peroxidase substrate is added to produce a detectable signal. For isolation purposes, a protein such as avidin that has affinity for biotin is conjugated to agarose beads. The biotin labeled metal-chelating moiety, after contacting a target zinc ion, is then incubated with the avidin beads, on a column or in solution, to separate and/or concentrate the zinc ions. A preferred form of biotin is the desthiobiotin analog, which can be easily adsorbed and released from avidin-based affinity matrices. A preferred form of avidin for some applications is CaptAvidin biotin-binding protein (Molecular Probes), which permits facile release of biotinylated compounds.

Haptens also include, among other derivatives, hormones, naturally occurring and synthetic drugs, pollutants, allergens, affector molecules, growth factors, chemokines, cytokines, lymphokines, amino acids, peptides, chemical intermediates, nucleotides and the like.

Fluorescent proteins also find use as labels for the zinc-binding compounds of the present invention. Examples of fluorescent proteins include green fluorescent protein (GFP) and the phycobiliproteins and the derivatives thereof. The fluorescent proteins, especially phycobiliproteins, are particularly useful for creating tandem dye-reporter molecules or for indirect detection of hapten-labeled zinc-binding compounds or zinc-binding proteins that are immobilized on a matrix, such as a microsphere or an array. These tandem dyes comprise a fluorescent protein and a fluorophore for the purposes of obtaining a larger Stokes shift, wherein the emission spectra are farther shifted from the wavelength of the fluorescent protein's absorption spectra. This property is particularly advantageous for detecting a low quantity of a target zinc ion in a sample wherein the emitted fluorescent light is maximally optimized; in other words, little to none of the emitted light is reabsorbed by the fluorescent protein. For this to work, the fluorescent protein and fluorophore function as an energy transfer pair wherein the fluorescent protein emits at the wavelength that the acceptor fluorophore absorbs and the fluorophore then emits at a wavelength farther from the fluorescent proteins than could have been obtained with only the fluorescent protein. Alternatively, the fluorophore functions as the energy donor and the fluorescent protein is the energy acceptor. Particularly useful fluorescent proteins are the phycobiliproteins disclosed in U.S. Pat. Nos. 4,520,110; 4,859,582; 5,055,556 and the fluorophore bilin protein combinations disclosed in U.S. Pat. No. 4,542,104. Alternatively, two or more fluorophore dyes can function as an energy transfer pair wherein one fluorophore is a donor dye and the other is the acceptor dye including any dye compounds disclosed in U.S. Pat. Nos. 6,358,684; 5,863,727; 6,372,445; 6,221,606; 6,008,379; 5,945,526; 5,863,727; 5,800,996; 6,335,440; 6,008,373; 6,184,379; 6,140,494 and 5,656,554.

d) Carrier Molecules

In an exemplary embodiment, the present compound is covalently bound to a carrier molecule, See Example 7. The carrier molecule can be attached the compound through either the chelating moiety or the reporter molecule, if present. If the compound has a reactive group, then the carrier molecule can alternatively be linked to the compound through the reactive group. The reactive group may contain both a reactive functional moiety and a linker, or only the reactive functional moiety.

A variety of carrier molecules are useful in the present invention. Exemplary carrier molecules include antigens, steroids, vitamins, drugs, haptens, metabolites, toxins, environmental pollutants, amino acids, peptides, proteins, nucleic acids, nucleic acid polymers, carbohydrates, lipids, and polymers. In another exemplary embodiment, at least one member selected from $R^1, R^2, R^3, R^4, R^5, R^6, R^7, R^8, R^9, R^{10}, R^{11}$, and $R^{12}$, is a carrier molecule or is attached to a carrier molecule. In one aspect at least one of $R^1, R^2, R^3, R^4, R^5, R^6, R^7$, and $R^8$ is a carrier molecule or is attached to a carrier molecule.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide. In a preferred embodiment the carrier molecule is amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell or a virus. In another preferred embodiment, the carrier molecule is an antibody or fragment thereof, an avidin or streptavidin, a biotin, a dextran, an IgG binding protein, a fluorescent protein, agarose, and a non-biological microparticle.

In another exemplary embodiment, the carrier molecule is an amino acid (including those that are protected or are substituted by phosphates, carbohydrates, or $C_1$ to $C_{22}$ carboxylic acids), or a polymer of amino acids such as a peptide or protein. In a related embodiment, the carrier molecule contains at least five amino acids, more preferably 5 to 36 amino acids. Exemplary peptides include, but are not limited to, neuropeptides, cytokines, toxins, protease substrates, and protein kinase substrates. Other exemplary peptides may function as organelle localization peptides, that is, peptides that serve to target the conjugated compound for localization within a particular cellular substructure by cellular transport mechanisms. Preferred protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the protein carrier molecule is an antibody, an antibody fragment, avidin, streptavidin, a toxin, a lectin, or a growth factor. Exemplary haptens include biotin, digoxigenin and fluorophores.

In another exemplary embodiment, the carrier molecule comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In another exemplary embodiment, the nucleotide carrier molecule is a nucleoside or a deoxynucleoside or a dideoxynucleoside.

Exemplary nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

In another exemplary embodiment, the carrier molecule comprises a carbohydrate or polyol that is typically a polysaccharide, such as dextran, FICOLL, heparin, glycogen, amylopectin, mannan, inulin, starch, agarose and cellulose, or is a polymer such as a poly(ethylene glycol). In a related embodiment, the polysaccharide carrier molecule includes dextran, agarose or FICOLL.

In another exemplary embodiment, the carrier molecule comprises a lipid (typically having 6-25 carbons), including glycolipids, phospholipids, and sphingolipids. Alternatively, the carrier molecule comprises a lipid vesicle, such as a liposome, or is a lipoprotein (see below). Some lipophilic substituents are useful for facilitating transport of the conjugated dye into cells or cellular organelles.

Alternatively, the carrier molecule is a cell, cellular systems, cellular fragment, or subcellular particles, including virus particles, bacterial particles, virus components, biological cells (such as animal cells, plant cells, bacteria, or yeast), or cellular components. Examples of cellular components that are useful as carrier molecules include lysosomes, endosomes, cytoplasm, nuclei, histones, mitochondria, Golgi apparatus, endoplasmic reticulum and vacuoles.

In another exemplary embodiment, the carrier molecule non-covalently associates with organic or inorganic materials. Exemplary embodiments of the carrier molecule that possess a lipophilic substituent can be used to target lipid assemblies such as biological membranes or liposomes by non-covalent incorporation of the dye compound within the membrane, e.g., for use as probes for membrane structure or for incorporation in liposomes, lipoproteins, films, plastics, lipophilic microspheres or similar materials.

e) Solid Supports

In an exemplary embodiment, the present compounds of the invention are covalently bonded to a solid support. The solid support may be attached to the compound either through the chelating moiety, reporter molecule, if present, or through a reactive group, if present, or through a carrier molecule, if present. Even if a reactive group, reporter molecule and/or a carrier molecule are present, the solid support may be attached through the chelating moiety. In another exemplary embodiment, at least one member selected from $R^1$, $R^2$, $R^3$, $R^4$, $R^5$, $R^6$, $R^7$, $R^8$, $R^9$, $R^{10}$, $R^{11}$, and $R^{12}$, is a solid support or is attached to a solid support. In one aspect, at least one of $R^1$, $R^2$, $R^3$, $R^4$, $R^5$, $R^6$, $R^7$, or $R^8$ is a solid support or is attached to a solid support A solid support suitable for use in the present invention is typically substantially insoluble in liquid phases. Solid supports of the current invention are not limited to a specific type of support. Rather, a large number of supports are available and are known to one of ordinary skill in the art. Thus, useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly (ethylene glycol)), nylon, latex bead, magnetic bead, paramagnetic bead, superparamagnetic bead, starch and the like.

In some embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the compounds of the invention. Useful reactive groups are disclosed above and are equally applicable to the solid support reactive functional groups herein.

A suitable solid phase support can be selected on the basis of desired end use and suitability for various synthetic protocols. For example, where amide bond formation is desirable to attach the compounds of the invention to the solid support, resins generally useful in peptide synthesis may be employed, such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (TentaGel™, Rapp Polymere, Tubingen, Germany), polydimethyl-acrylamide resin (available from Milligen/Biosearch, California), or PEGA beads (obtained from Polymer Laboratories).

C. Combination of Components to Form Zinc-Binding Compounds

The components of the zinc-binding compound having now been described, combination of certain reporter molecules, linkers and the metal chelating moiety are provided to demonstrate the complexity of the zinc-binding compounds and their application. While it has been stressed that a wide range of components can be used to make the zinc-binding compounds it should also be understood that the individual selection of components to make a particularly useful zinc-binding compound for detection purposes requires an understanding of the reporter molecules, carrier molecules, reactive group, solid supports, the linkers, the acetic acid analogs of BAPTA and how certain combinations, and substituents function to selectively bind to physiological concentrations of zinc ions in the presence of physiological concentrations of calcium ions or other non-target metal ions.

While a wide range of zinc-binding compounds are contemplated it is understood that the compounds represented by the following formula is not part of the present invention:

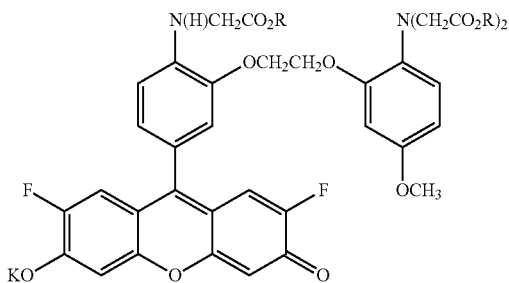

wherein R is H, a salt ion or an AM ester represented by CH$_2$OC(O)CH$_3$.

However, as discussed above a particularly useful combination are dyes that localize at the mitochondrial membrane with a chelating moiety of the present invention. Because the chelating moiety is capable of binding physiological concentration of zinc ions in the presence of physiological concentrations of calcium ions, ions that are both present and both have a role in mitochondrial function and associated functions, this combination provides a useful tool for selectively measuring zinc ions at the mitochondrial interface. Examples of these compounds include compounds 4 and 5 as well as the following compound.

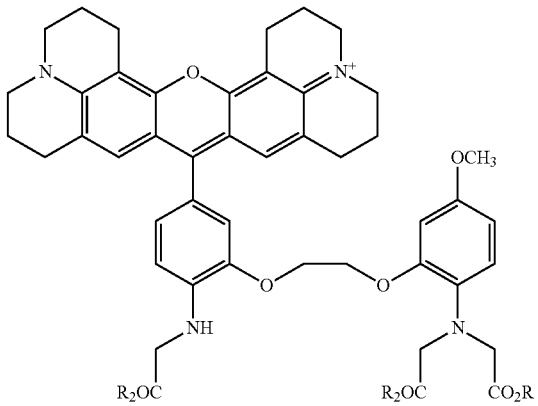

Compound 6

In addition, other dye compounds that either localize to different cellular organelles or ones that are not selective for such organelles, i.e. remain in the cytosol, are useful for other applications. It is appreciated that the assay design will dictate the reporter molecule or carrier molecule that is combined with the chelating moiety and that the substituents on the reporter molecule or chelating moiety including the choice of a linker is determined depending on the intended use.

In a further embodiment, compounds that comprise a carrier molecule are also contemplated and find utility in binding zinc-ions. In one aspect, the compound is

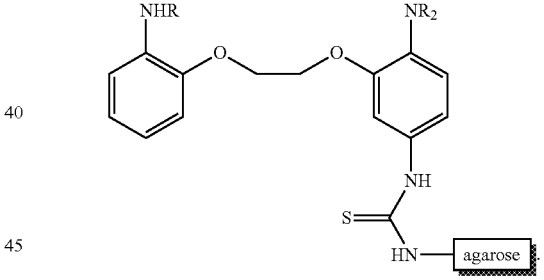

Compound 20

Methods of Use

The zinc-binding compounds of the present invention are useful for any application where it is desirable to complex a target metal ion ($Zn^{2+}$, $Ca^{2+}$ or $Fe^{2+}$). Thus, the present compounds may be utilized without limit for the detection, monitoring, quantitation, binding and isolating of zinc ions. Selected zinc-binding compounds of the invention may be useful as ionophores, that is, they facilitate the transport of selected target ions across cell membranes. Where the zinc-binding compound is bound to a carrier molecule or solid support that is a polymeric matrix, such as a microparticle, dextran, polystyrene or agarose, the compounds are useful for depleting a sample solution, sequestering, of a selected target ion, particularly where the polymeric matrix is used to pack a chromatography column. Other zinc-binding compounds (those bound to a reporter molecule) are useful as fluorescent, colorimetric or fluorometric indicators for a selected target ion. This new class of zinc-binding compounds, acetic acid analogs of BAPTA, can be used in any of the same assays previously described for zinc indicators.

In an exemplary embodiment, the present zinc-binding compounds are chemically reactive wherein the compound is covalently attached to a reactive group. In this way the chemically reactive zinc-binding compounds can be conjugated to a desired reporter molecule, carrier molecule or solid support, which may be selected from any of the above disclosed molecules and groups. The specific zinc-binding compound used in an assay or experiment is selected based on the desired affinity for the target zinc ion as determined by the expected concentration range in the sample, the desired end result, (e.g., binding, isolating or detecting), the desired live cell properties and the desired selectivity. These chemically reactive zinc-binding compounds allow for the end user to tailor the compound to their desired experiment.

In one aspect of the invention, a chemically reactive zinc-binding compound is combined with a reporter molecule, carrier molecule or solid support under appropriate conditions to form a covalent bond. Methods of forming a conjugate between a chemically reactive compound and a substance to be conjugated are well documented in the art and generally known to one of skill in the art (including U.S. Pat. No. 5,453,517). The acetic acid analogs of BAPTA/reactive group compounds of the invention are typically first dissolved in water or a water-miscible such as a lower alcohol, dimethylformamide (DMF), dimethylsulfoxide (DMSO), acetone, acetonitrile, tetrahydrofuran (THF), dioxane or acetonitrile. These preparations are well documented in Haugland, *Molecular Probes, Inc. Handbook of Fluorescent Probes and Research Chemicals*, (9$^{th}$ ed., September 2002) and Brinkley, *Bioconjugate Chem.*, 3: 2 (1992). Conjugates typically result from mixing appropriate reactive compounds and the component to be conjugated in a suitable solvent in which both are soluble, using methods well known in the art, followed by separation of the conjugate from any unreacted component and by-products. These present compounds are typically combined with the component under conditions of concentration, stoichiometry, pH, temperature and other factors that affect chemical reactions that are determined by both the reactive groups on the compound and the expected site of modification on the component to be modified. These factors are generally well known in the art of forming bioconjugates (Haugland et al., "Coupling of Antibodies with Biotin", *The Protein Protocols Handbook*, J. M. Walker, ed., Humana Press, (1996); Haugland "Coupling of Monoclonal Antibodies with Fluorophores", *Methods in Molecular Biology*, Vol. 45: *Monoclonal Antibody Protocols*, W. C. Davis, ed. (1995)). For those reactive compounds that are photoactivated, conjugation requires illumination of the reaction mixture to activate the reactive compound. The conjugated component is used in solution or lyophilized and stored for later use.

In an exemplary embodiment, the present compounds comprise a carrier molecule or a solid support. In one aspect the carrier molecule or solid support facilitates the binding and sequestration of zinc ions from a solution. This has utility wherein it is desirable to deplete a solution of zinc ions, such as the commercially available Calcium Sponge (Molecular Probes, Inc.) for the removal of calcium ions from solution. The present compounds may be conjugated to any solid support such that when a solution contain zinc ions comes into contact with the present zinc-binding compounds the zinc ions are bound while the sample solution is allowed to pass freely by the immobilized zinc-binding compounds. Once the zinc-binding compounds have been saturated, the zinc ions can be released from the zinc-binding compounds by combining with an appropriate buffer to regenerate the zinc-binding conjugates. Appropriate buffers that are useful for releasing zinc ions from the present compounds include solutions of tetrakis-(2-pyridylmethyl)ethylenediamine (TPEN). After the removal of the zinc ions, additional sample solution may be passed over the immobilized zinc-binding compounds to further remove zinc ions.

In one aspect, the zinc-binding compounds are conjugated to a polymer such as a microparticle, dextran, agarose, acrylamide, polystyrene, see Example 7 Compound 20. These conjugates are useful to pack into a column wherein a sample solution may be run through the column to remove undesirable zinc-ions. These conjugates are also useful for isolating and concentrating zinc ions. In this way the column may become saturated a number of times and zinc-ions repeatedly released to form a concentrated pool of zinc ions.

In another aspect, the present compounds are conjugated to a protein such as an antibody. In this way the zinc-binding compounds are selectively localized to a target wherein zinc ions are bound and optionally detected when the compound also comprises a reporter molecule.

In one embodiment, the compounds of the invention, in any of the embodiments described above, are associated, either covalently or noncovalently, with a solid support and a reporter molecule. The solid support includes, without limitation, a microfluidic chip, a silicon chip, a microscope slide, a microplate well, or another solid matrix, wherein the acetic acid analog of BAPTA/solid support/reporter molecule compound is combined with the sample of interest as it flows over the surface. The detectable optical response is therefore detected on the matrix surface itself, typically by use of an instrument. This embodiment of the invention is particularly suited to high-throughput screening and/or high content screening using automated methods, as disclosed in U.S. Pat. No. 6,127,133.

In a related embodiment, the present compounds form a complex with a target metal ion. Preferably, the metal ion is zinc. In addition, this complex can further comprise a molecule that has affinity for the target ion, such as a zinc-binding protein, to form a ternary complex.

In an exemplary embodiment the present compounds are used to detect zinc ions wherein the acetic acid analog of BAPTA is covalently attached to a reporter molecule. This covalent attachment may involve shared atoms of ring A or ring B of the acetic acid analog of BAPTA, a single covalent bond or a series of stable covalent bonds. Only the latter is typically a result of a conjugation reaction, i.e., a chemically reactive zinc-binding compound reacting with a chemically reactive reporter molecule to form a zinc-binding compound/reporter molecule conjugate. Zinc-binding compounds comprising a reporter molecule with no linker or a single covalent bond are usually formed during the synthesis of the acetic acid analog of BAPTA.

In one aspect of the invention, for a particular zinc-binding compound of the present invention to be useful for detection purposes, it must exhibit a detectable change in spectral properties upon complexation of the desired metal ion (target ion) in the chelating moiety. This is necessary when zinc-binding compounds complexed with zincs cannot be separated from zinc-binding compounds that are not bound to zinc. Preferably the change in spectral properties is a change in fluorescence properties. More preferably, the instant compounds display an intensity increase or decrease in emission energy upon the complexation of the desired target ion. Zinc-binding compounds that comprise a reporter molecule that is colorimetric or fluorometric are herein referred to as "indicators".

Alternatively, a change in spectral properties upon binding of a target ion is not necessary wherein a stable ternary complex is formed. Typically this ternary complex is immobilized allowing for the removal of unbound zinc-binding compounds.

Initially, the suitability of a zinc-binding compound as an indicator of zinc ion concentration is commonly tested by mixing a constant amount of the indicator with a measured amount of the target ion under the expected experimental conditions.

In general, this colorimetric or fluorometric method comprises combining zinc-binding compounds of the present invention with a sample for a sufficient time to allow said compounds to bind zinc ions whereby zinc ions are bound. Following binding of the present zinc ions, the sample is illuminated with an appropriate light source and the signal correlated with the known concentration of zinc ions. This titration curve is then used to experimentally determine the appropriate zinc-binding compound for a particular assay.

Preferred indicators display a high selectivity, that is, they show a sufficient rejection of non-target ions. The interference of a non-target ion is tested by a comparable titration of the indicator with that ion. Although preferred target ions for most indicators of the present invention are $Zn^{2+}$ and $Ca^{2+}$, any ion that yields a detectable change in absorption wavelengths, emission wavelengths, fluorescence lifetimes or other measurable optical property over the concentration range of interest is potentially measured using one of the indicators of this invention. Modifications to the electronic structure of the acetic acid an analog of BAPTA or reporter molecule produce a zinc-binding compound having the appropriate combination of binding affinity, ion selectivity and spectral response for a wide variety of metal ions.

After an appropriate zinc-binding compound is determined, the experiment of choice is carried out wherein the sample typically comprises biological fluids or live cells. When the sample is a biological fluid the zinc-binding compound is water soluble and generally stored in a concentrated organic solvent such as dimethylsulfoxide (DMSO). When the sample comprises live cells and the intent is to measure intracellular zinc ions the zinc-binding compounds typically comprise at least one AM ester group ($CH_2OC(O)CH_3$) or an alternative lipophilic group that facilitates entry into live cells. The AM ester zinc-binding compounds are not water-soluble and are generally stored in lyophilized form. Alternatively, zinc-binding compounds of the present invention can be used to measure intracellular zinc ion concentrations that do no comprise a lipophilic group wherein the zinc binding compounds are loaded into cells by mechanical means such as microinjection.

Thus, a method for binding and detecting target ions in a live cell comprises the following steps:
a) contacting a sample of live cells with a zinc-binding compound of the present invention wherein said compound comprises a reporter molecule and at least one lipohilic group;
b) incubating said sample and said zinc-binding compound for sufficient time to allow said compound to chelate said target metal ion; and,
c) illuminating said sample with an appropriate wavelength whereby said target ion is detected in a live cell.

Therefore, in an exemplary embodiment, compounds useful for detecting zinc ions in a live cell contain at least one —($CH_2OC(O)CH_3$) group or lipophilic group. Typically, the zinc-binding compound is a triacetic acid analog of BAPTA wherein exactly one of $R_X$, $R_Y$, $R_X'$ or $R_Y'$ is hydrogen, and the remaining $R_X$, $R_Y$, $R_X'$ or $R_Y'$ are —$CH_2CO_2R$, wherein R is $CH_2OC(O)CH_3$. In a further aspect, the compound typically comprises a reporter molecule that is a fluorophore wherein at least one of $R^1$-$R^8$ is a fluorophore. Preferably $R^3$ or $R^6$ is a xanthene fluorophore. Alternatively, the fluorophore may be substituted by a lipophilic group including, but not limited to, an AM ester.

For methods designed to measure zinc ions associated with the mitochondria the method typically comprises combining a zinc-binding compound of the present invention with a sample comprising live cells wherein the reporter molecule is a cationic dye and the chelating moiety typically comprises at least one AM ester group. Preferably the cationic dye is a derivative of 3-aminoxanthene-6-imine, specifically Compound 4 or 5, but any dye disclosed in U.S. Pat. Nos. 5,459, 268; 5,686,261 and 6,291,203 may be used.

Thus, in one embodiment of the invention, the sample contains cells, and the zinc-binding compound is combined with the sample in such a way that the zinc-binding compound is present within the sample cells. By selection of the appropriate chelating moiety, fluorophore, and the substituents thereon, indicators are prepared that will selectively localize in desired organelles, and provide measurements of the target ion in those organelles. Conjugates of the indicators of the invention with organelle-targeting peptides are used to localize the indicator to the selected organelle, facilitating measurement of target ion presence or concentration within the organelle (as described in U.S. Pat. No. 5,773,227). Alternatively, selection of a lipophilic fluorophore, or a fluorophore having predominantly lipophilic substituents will result in localization in lipophilic environments in the cell, such as cell membranes. As described above, selection of cationic zinc-binding compound will typically result in localization of the indicator in mitochondria. Alternatively, selection of reporter molecules that facilitates localization to a different region or compartment of the cell such as the nucleus, liposome or an acidic compartment may be used. These reporter molecules include any of the compounds disclosed in U.S. Pat. Nos. 5,869,689; 6,664,047; 5,436,134; 5,658,751 and 5,863,753.

A preferred zinc-binding compound for zinc ions is a compound that shows at least a two-fold change in net fluorescence emission intensity (either higher or lower), or a 1 nanosecond difference in fluorescence lifetime (either shorter or longer), preferably a five-fold or greater change in net fluorescence emission intensity or a 100% change in fluorescence lifetime in response to the target ion. Most preferred is a compound that demonstrates a 10-100-fold change in net fluorescence emission intensity. Alternatively, an zinc-binding compound that exhibits a shift in excitation or emission wavelength of at least 10 nm (either to shorter or longer wavelength) is also preferred, more preferably exhibiting a shift of 25 nm or greater.

The optical response of the zinc-binding compound is determined by changes in absorbance or fluorescence, preferably fluorescence. If absorbance measurements are used to determine ion concentrations, then it is usually optimal to adjust the optical density of the zinc-binding compound in the sample over the range of analyte concentration to a value of approximately 0.02 to 2.5 (most preferably 0.1 to 1). For fluorescence measurements, the concentration of the zinc-binding compound will depend mostly on the sensitivity of the equipment used for its detection.

If the optical response of the indicator will be determined using fluorescence measurements, samples are typically stained with zinc-binding compound concentrations of about $10^{-9}$ M to $10^{-2}$ M, more typically with concentrations of about $10^{-7}$ M to $10^{-3}$ M. The most useful range of analyte concentration is about one log unit above and below the dissociation constant of the ion/acetic acid analog of BAPTA complex. This dissociation constant is determined by titration of the indicator with a known concentration of the target ion, usually over the range of virtually zero concentration to approximately 100 millimolar of the target ion, depending on which ion is to be measured and which zinc-binding compound is being used. The dissociation constant may be affected by the presence of other ions, particularly ions that have similar ionic radii and charge. It may also be affected by other conditions such as ionic strength, pH, temperature, viscosity, presence of organic solvents and incorporation of the sensor in a membrane or polymeric matrix, or conjugation or binding of the sensor to a protein or other biological molecule. Any or all of these effects need to be taken into account when calibrating a present zinc-binding compound.

The zinc-binding compound is combined with a sample in a way that will facilitate detection of the target ion concentration in the sample. The sample is generally a representative cell population, fluid or liquid suspension that is known or suspected to contain the target ion. Representative samples include intracellular fluids such as in blood cells, cultured cells, muscle tissue, neurons and the like; extracellular fluids in areas immediately outside of cells; in vesicles; in vascular tissue of plants and animals; in biological fluids such as blood, saliva, and urine; in biological fermentation media; in environmental samples such as water, soil, waste water and sea water; in industrial samples such as pharmaceuticals, foodstuffs and beverages; and in chemical reactors. Detection and quantitation of the target ion in a sample can help characterize the identity of an unknown sample, or facilitate quality control of a sample of known origin.

The sample can be a biological fluid such as whole blood, plasma, serum, nasal secretions, sputum, saliva, urine, sweat, transdermal exudates, cerebrospinal fluid, or the like. Biological fluids also include tissue and cell culture medium wherein zinc ions have been secreted into the medium. Alternatively, the sample may be whole organs, tissue or cells from the animal. Examples of sources of such samples include muscle, eye, skin, gonads, lymph nodes, heart, brain, lung, liver, kidney, spleen, thymus, pancreas, solid tumors, macrophages, mammary glands, mesothelium, and the like. Cells include without limitation prokaryotic cells and eukaryotic cells that include primary cultures and immortalized cell lines. Eukaryotic cells include without limitation ovary cells, epithelial cells, circulating immune cells, β cells, hepatocytes, and neurons. Zinc ions have been determined to play a role in many mammalian, if not all, organs and cell types such that there is no intended limitation on the sample for the present invention.

The end user will determine the choice of the sample and the way in which the sample is prepared. The sample includes, without limitation, any biological derived material that is thought to contain zinc ions. Alternatively, samples also include material that zinc ions have been added to determine the effect the zinc ions have on predetermined biological parameters.

Quantification of target ion levels in samples is typically accomplished using the zinc-binding compounds of the present invention by methods known in the art. For example, the ratiometric measurement of ion concentration provides accurate measurement of ion concentrations by the treatment of the fluorescence data as the ratio of excitation or fluorescence intensities at two wavelengths, rather than the absolute intensity at a single wavelength. This method is exemplified by the use of Compound 13. Using the ratio method, a number of variables that may perturb the ion concentration measurements are eliminated. In particular, ion-dependent factors that affect the signal intensity, such as nonuniform intracellular dye concentrations, probe leakage, dye bleaching and cell thickness, are canceled in the ratio measurements, since these parameters have a similar effect on intensities at both wavelengths. While the ratio method can be used to determine concentrations using observation of either the excitation spectra of the indicator, the emission spectra of the indicator, or both, in the case of the indicators of the present invention, the shift in excitation energy upon binding metal ions makes observation of the excitation spectrum a more useful technique. In either case, to achieve maximal utility, the indicator must be calibrated (to compensate for variance in the dissociation constant of the indicator due to ionic strength, viscosity, or other conditions within the sample). To calibrate the indicator, ionophores such as A-23187, gramicidin, valinomycin, or ionomycin are used. Non-ratiometric analysis can also be accomplished by calibration with a second fluorescent dye present in the sample.

The optical response of the indicator to the ion can be detected by various means that include measuring absorbance or fluorescence changes with an instrument, visually, or by use of a fluorescence sensing device. At any time during and after binding zinc-ions, the sample is illuminated with a wavelength of light selected to give a detectable optical response, and observed with a means for detecting the optical response. Equipment that is useful for illuminating the zinc-binding compounds of the present invention includes, but is not limited to, hand-held ultraviolet lamps, mercury arc lamps, xenon lamps, lasers and laser diodes. These illumination sources are optically integrated into laser scanners, fuorescences microplate readers or standard or microfluorometers. The degree and/or location of zinc binding, compared with a standard or expected response, indicates whether and to what degree the sample possesses a given characteristic, i.e. concentration of zinc ions is response to a stimulus.

The optical response is optionally detected by visual inspection, or by use of any of the following devices: CCD camera, video camera, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

Alternatively, these measurements may be made remotely by incorporation of the fluorescent ion sensor as part of a fiber optic probe. The indicator is covalently attached to the fiber optic probe material, typically glass or functionalized glass (e.g., aminopropyl glass) or the indicator is attached to the fiber optic probe via an intermediate polymer, such as polyacrylamide. The indicator solution is alternatively incorporated non-covalently within a fiber optic probe, as long as there is a means whereby the target ion can come into contact with the indicator solution.

The foregoing methods having been described it is understood that the many and varied compounds of the present invention can be utilized with the many methods. The compounds not being limited to just those that are specifically disclosed.

Therefore, in an exemplary embodiment, the present methods utilize compounds wherein exactly one of said $R_X$, $R_Y$, $R_{X'}$ or $R_{Y''}$ is hydrogen or $C_1$-$C_6$ alkyl. In one aspect, exactly one of said $R_X$, $R_Y$, $R_{X'}$ or $R_{Y''}$ is hydrogen and the remaining $R_X$, $R_Y$, $R_{X'}$ or $R_{Y''}$ are —$CH_2CO_2R$ wherein R is H, a salt ion or $CH_2OC(O)CH_3$. In one embodiment R is H or a salt ion. In another embodiment R is $CH_2OC(O)CH_3$.

In an exemplary embodiment, the methods utilize compounds that are useful for detecting zinc-ions. In this instance the compounds comprise at least one reporter group, preferably the methods utilize a compound wherein at least one of $R^1$-$R^8$ is a reporter molecule; more preferably at least one of $R^3$ or $R^6$ is a reporter molecule. The reporter molecule is selected from the group consisting of a chromophore, fluorophore, fluorescent protein, phosphorescent dye or a tandem dye. In one aspect, the compounds comprise a reporter molecule that is a fluorophore selected from the group consisting of dansyl, xanthene, cyanine, borapolyazaindacene, pyrene, naphthalene, coumarin, oxazine, benzofuran, quinazolinone, indole, benzazole or derivatives thereof. These reporter molecules are independently substituted by substituents selected from the group consisting of hydrogen, halogen, amino, substituted amino, alkyl, substituted alkyl, aryl, substituted aryl, heteroaryl, substituted heteroaryl, alkoxy, sulfo, reactive group and carrier molecule.

In one aspect, the compounds of the methods comprise a fluorophore that is a xanthene dye selected from the group consisting of fluorescein or derivative thereof, rhodamine or derivative thereof, rhodol or derivative thereof or rosamine or a derivative thereof.

In an exemplary embodiment, the reporter molecule is a 3-aminoxanthene-6-imine. In one aspect the methods utilize a compound that is

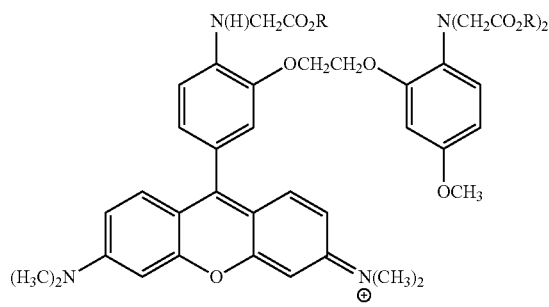

with a biologically compatible anion.

In another exemplary embodiment, the compounds of the methods comprise a reactive group, solid support or carrier molecule either with or without the compound further comprising a reporter molecule. The reactive group, solid support, carrier molecule and optionally the reporter molecule comprise a linker that is a single covalent bond, or a covalent linkage that is linear or branched, cyclic or heterocyclic, saturated or unsaturated, having 1-20 nonhydrogen atoms selected from the group consisting of C, N, P, O and S; and are composed of any combination of ether, thioether, amine, ester, carboxamide, sulfonamide, hydrazide bonds and aromatic or heteroaromatic bonds. Alternatively, the reporter group, such as benzofuran, does not comprise a linker, but instead shares atoms with the ring A or ring B of the acetic acid analog of BAPTA.

Thus, in one embodiment of the methods the compounds comprise a reactive group that is useful for forming conjugates to reporter molecules, solid supports and/or carrier molecules. The reactive groups are selected from the group consisting of an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a halotriazine, a hydrazine, an imido ester, an isocyanate, an isothiocyanate, a maleimide, a phosphoramidite, a reactive platinum complex, a silyl halide, a sulfonyl halide, a thiol and a photoactivatable group. In one aspect, the reactive group is selected from the group consisting of carboxylic acid, succinimidyl ester of a carboxylic acid, hydrazide, amine and a maleimide.

In another embodiment of the methods the compounds comprise a carrier molecule selected from the group consisting of an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell or a virus. In one aspect, the carrier molecule is selected from the group consisting of an antibody or fragment thereof, an avidin or streptavidin, a biotin, a dextran, an IgG binding protein, a fluorescent protein, agarose, and a non-biological microparticle.

In yet another embodiment of the methods, the compound comprise a solid support selected from the group consisting of a microfluidic chip, a silicon chip, a microscope slide, a microplate well, silica gels, polymeric membranes, particles, derivatized plastic films, glass beads, cotton, plastic beads, alumina gels, polysaccharides, polyvinylchloride, polypropylene, polyethylene, nylon, latex bead, magnetic bead, paramagnetic bead, and superparamagnetic bead. In one aspect, the solid support is selected from the group consisting of Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose and starch.

Kits

Suitable kits for binding, detecting and identifying enzymes and or pathways that are involved regulating biological zinc ion concentrations also form part of the invention. Such kits can be prepared from readily available materials and reagents and can come in a variety of embodiments. The contents of the kit will depend on the design of the assay protocol or reagent for detection or measurement. All kits will contain instructions, zinc-binding compounds and appropriate reagents, as needed. Typically, instructions include a tangible expression describing the reagent concentration or at least one assay method parameter such as the relative amounts of reagent and sample to be added together, maintenance time periods for reagent/sample admixtures, temperature, buffer conditions and the like to allow the user to carry out any one of the methods or preparations described above.

Therefore, kits of the present invention comprise at least one zinc-binding compound of the present invention in an appropriate storage form, e.g. lyophilized or dissolved in an organic solvent, and instructions for preparing the zinc-binding compound to be used by the end user. In addition, the kits may contain appropriate controls (including a positive control), metal ion calibration standards, buffer solutions and additional detection reagents such as calcium indicators, organelle stains, a metal ion indicator other than for zinc ions, an antibody or fragment thereof or a reference dye standard.

In an exemplary embodiment, the kits contain compounds wherein exactly one of said $R_X$, $R_Y$, $R_{X'}$ or $R_{Y'}$ is hydrogen or $C_1$-$C_6$ alkyl. In one aspect, exactly one of said $R_X$, $R_Y$, $R_{X'}$ or $R_{Y'}$ is hydrogen and the remaining $R_X$, $R_Y$, $R_{X'}$ or $R_{Y'}$ are —$CH_2CO_2R$ wherein R is H, a salt ion or $CH_2OC(O)CH_3$. In one embodiment R is H or a salt ion. In another embodiment R is $CH_2OC(O)CH_3$.

In one aspect the kits contain compounds that are useful for detecting zinc-ions. In this instance the compounds comprise at least one reporter group, preferably the kit contains a compound wherein at least one of $R^1$-$R^8$ is a reporter molecule; more preferably at least one of $R^3$ or $R^6$ is a reporter molecule. The reporter molecule is selected from the group consisting of a chromophore, fluorophore, fluorescent protein, phosphorescent dye or a tandem dye. In one aspect, the compounds comprise a reporter molecule that is a fluorophore selected from the group consisting of dansyl, xanthene, cyanine, borapolyazaindacene, pyrene, naphthalene, coumarin, oxazine, benzofuran, quinazolinone, indole, benzazole or derivatives thereof. These reporter molecules are independently substituted by substituents selected from the group consisting of hydrogen, halogen, amino, substituted amino, alkyl, substituted alkyl, aryl, substituted aryl, heteroaryl, substituted heteroaryl, alkoxy, sulfo, reactive group and carrier molecule.

In one embodiment, the compounds in the kit comprise a fluorophore that is a xanthene dye selected from the group consisting of fluorescein or derivative thereof, rhodamine or derivative thereof, rhodol or derivative thereof or rosamine or a derivative thereof.

In an exemplary embodiment, the reporter molecule is a 3-aminoxanthene-6-imine. In one aspect the kits comprise a compound that is

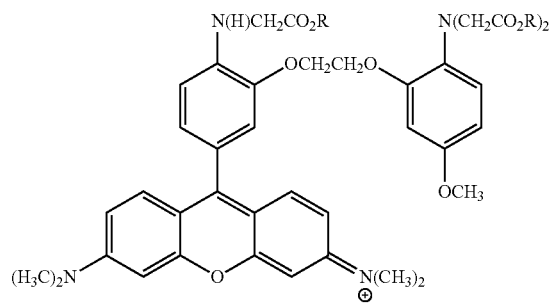

with a biologically compatible anion.

In another exemplary embodiment, the compounds of the kits comprise a reactive group, solid support or carrier molecule either with or without the compound further comprising a reporter molecule. The reactive group, solid support, carrier molecule and optionally the reporter molecule comprise a linker that is a single covalent bond, or a covalent linkage that is linear or branched, cyclic or heterocyclic, saturated or unsaturated, having 1-20 nonhydrogen atoms selected from the group consisting of C, N, P, O and S; and are composed of any combination of ether, thioether, amine, ester, carboxamide, sulfonamide, hydrazide bonds and aromatic or heteroaromatic bonds. Alternatively, the reporter group, such as benzofuran, does not comprise a linker, but instead shares atoms with the ring A or ring B of the acetic acid analog of BAPTA.

Thus, in one embodiment of the kits the compounds comprise a reactive group that is useful for forming a conjugate with a reporter molecule, carrier molecule and/or solid support. The reactive group is selected from the group consisting of an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a halotriazine, a hydrazine, an imido ester, an isocyanate, an isothiocyanate, a maleimide, a phosphoramidite, a reactive platinum complex, a silyl halide, a sulfonyl halide, a thiol and a photoactivatable group. In one aspect, the reactive group is selected from the group consisting of carboxylic acid, succinimidyl ester of a carboxylic acid, hydrazide, amine and a maleimide.

In another embodiment of the kits the compounds comprise a carrier molecule selected from the group consisting of an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell or a virus. In one aspect, the carrier molecule is selected from the group consisting of an antibody or fragment thereof, an avidin or streptavidin, a biotin, a dextran, an IgG binding protein, a fluorescent protein, agarose, and a non-biological microparticle.

In yet another embodiment of the kits, the compound comprise a solid support selected from the group consisting of a microfluidic chip, a silicon chip, a microscope slide, a microplate well, silica gels, polymeric membranes, particles, derivatized plastic films, glass beads, cotton, plastic beads, alumina gels, polysaccharides, polyvinylchloride, polypropylene, polyethylene, nylon, latex bead, magnetic bead, paramagnetic bead, and superparamagnetic bead. In one aspect, the solid support is selected from the group consisting of Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose and starch.

A detailed description of the invention having been provided above, the following examples are given for the purpose of illustrating the invention and shall not be construed as being a limitation on the scope of the invention or claims.

EXAMPLES

Example 1

Synthesis of Compound 4 and 5

Condensation of the aldehyde 1 (Gee K R, et al. *J Am Chem Soc* (2002) 124:776-778) with two equivalents of 3-dimethylaminophenol afforded the unstable dihydroxanthene 2, which was quickly oxidized with ρ-chloranil to give the xanthene 3. The methyl esters were removed by saponification, and the resulting salt form of 4 converted into its cell permeable AM ester (Tsien R Y, *Nature* (1981) 290:527-528) form 5 by acidification and reaction with bromomethyl acetate. Compound 4 and 5 utilizes the cationic rhodamine fluorophore (Minta A, et al., *J Biol Chem* (1989) 264: 8171-8), coupled to the N,N,N'-triacetic acid chelator contained in the zinc fluoroionophore FluoZin-3 (Gee K R, et al. *J Am Chem Soc* (2002) 124: 776-778 (supra); Gee K R, et al., *Cell Calcium* (2002) 31: 245-51).

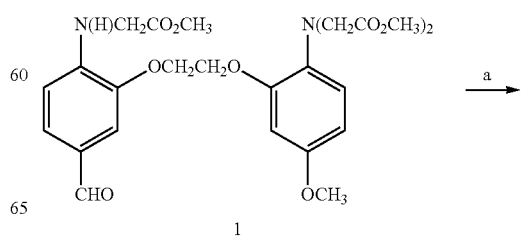

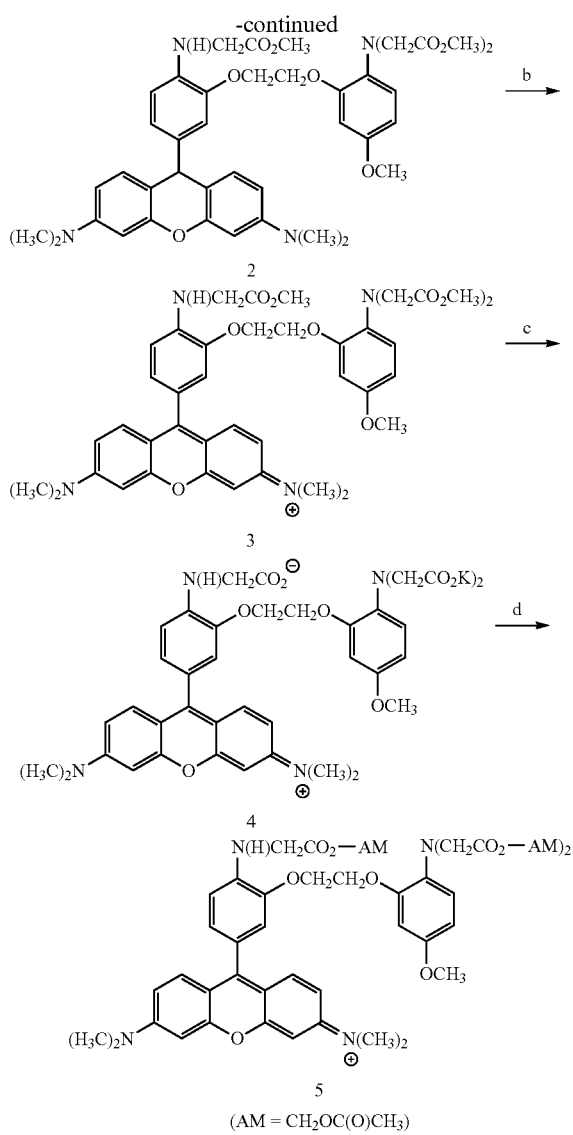

Example 2

Increased Fluorescence Upon Binding of Zinc Ions in Solution by Compound 4

Titration of Compound 4 with buffered $Zn^{2+}$ solutions in a cuvet revealed that Compound 4 is essentially non-fluorescent but becomes brightly fluorescent orange as the $Zn^{2+}$ concentration is increased. Absorption and emission spectra, dissociation constants, and fluorescence enhancements were measured in standard fashion (Haugland R P. Handbook of Fluorescent Probes and Research Products, Ch. 20, supra). Spectra were measured at 22° C. in 100 mM KCl, 50 mM MOPS, pH 7.0. A 75-fold fluorescence increase was observed as the solution goes from TPEN (no $Zn^{2+}$) to saturating $Zn^{2+}$, and a dissociation constant ($K_D$) of 65±10 nM was observed (see FIG. 1). No $Ca^{2+}$ sensitivity is observed at $\leq 40$ µM. Free $[Zn^{2+}]$ in buffered solutions was determined using WEB-MAXC v2.10. Free $Zn^{2+}$ solutions of 0.7 nM, 2.75 nM, and 11 nM were prepared using 0.2 mM, 0.5 mM, and 0.8 mM, respectively, zinc chloride in 1 mM EGTA. Free $Zn^{2+}$ solutions of 27 nM, 109 nM, 436 nM, 974 nM, and 1.9 µM were prepared using 0.2 mM, 0.5 mM, 0.8 mM, 0.9 mM, and 0.95 mM, respectively, zinc chloride in 1 mM of the weaker chelator ADA (N-(2-acetamido)iminodiacetic acid).

Screening of Compound 4 against other metal ion solutions revealed modest sensitivity to $Fe^{3+}$ ($K_D \sim 5$ µM), very weak sensitivity to 500 µM $Hg^{2+}$ and 500 µM $Cd^{2+}$, and no response to 500 µM $Pb^{2+}$, $Ni^{2+}$, $Mn^{2+}$, $Mg^{2+}$, $Ga^{3+}$, or 200 mM $Na^+$. $Fe^{2+}$ and $Cu^{2+}$ completely quenched the fluorescence of Compound 4, as is normal with paramagnetic metals.

Example 3

Localization of Compound 5 in Live Cell Mitochondria

Figure 2:
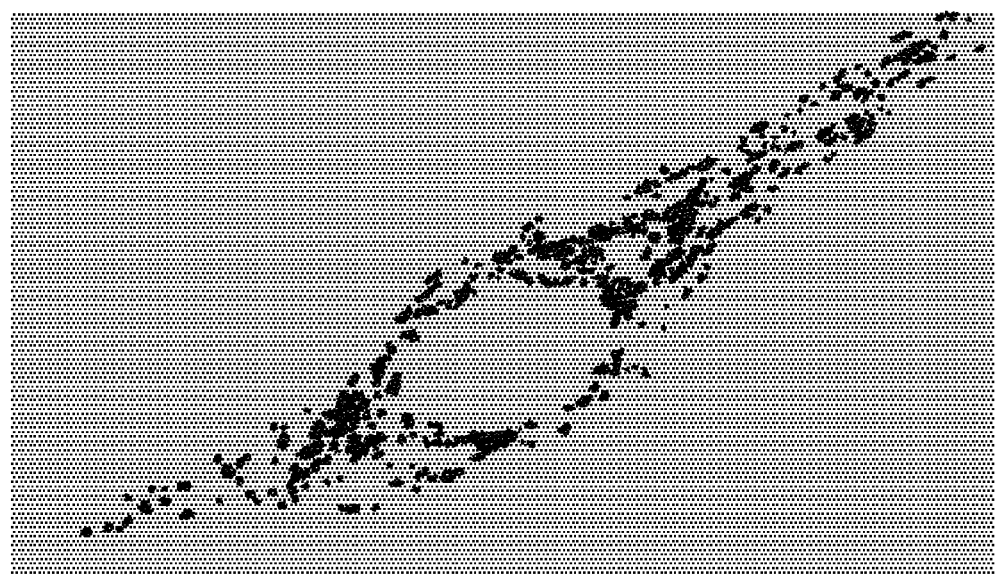
FIG. 2: Shows the Co-localization of Compound 5 and the mitochondrial selective probe MITOTRACKER® Green FM dye. Cultures were co-loaded with Compound 5 (red fluorescence) and the mitochondrial marker, MITOTRACKER Green FM dye (green fluorescence), and imaged with confocal laser-scanning microscopy. Note the substantial overlap between the probes (yellow), indicating that they largely target the same intracellular organelles. Bar=10 μm. See, Example 3.

To verify that Compound 5 effectively localizes into mitochondria, cortical neurons were loaded with the AM ester of Compound 4 (Compound 5; 10 µM+0.1% Pluronic F127 at 4° C. for 30 min and then left at 37° C. for 4 h for de-esterification) and the mitochondrial marker, MITOTRACKER Green FM (Molecular Probes, Inc.) (Collins T J, et al. *EMBO J.* (2002); 21: 1616-27; Buckman J F, et al. *J Neurosci Methods* (2001) 104:165-76; U.S. Pat. Nos. 5,459,268 and 5,686,261). For neuronal imaging, murine forebrain cultures, derived from E-15 embryos, were plated on previously established astrocytic monolayers and used between 13 and 16 days in vitro (Yin H Z, et al. *Neuroreport* (1995) 6: 2553-6). When co-loaded with MITOTRACKER Green FM (200 nM, 37° C., 30 min), neurons showed a strong co-localization of these probes, with distinct speckled pattern of fluorescence, most prominent in the perinuclear region, characteristic of mitochondria staining (see FIG. 2).

Experiments were carried out using a simplified $Ca^{2+}$-free HEPES-buffered medium (HSS) whose composition was (in mM): 120 NaCl, 5.4 KCl, 0.8 $MgCl_2$, 20 HEPES, 15 glucose, 10 NaOH, pH 7.4. Series of confocal images (7 planes each 2 µm deep) were obtained using either an Olympus fluoview (Olympus USA, Melville, N.Y.), or a Bio-Rad MRC 600 (Bio-Rad Laboratories; Hercules, Calif.) confocal system equipped with 60× and 40× objectives respectively, and argon (Ex: 488 nm; Em: >510 nm, for MITOTRACKER Green FM) and krypton (Ex: 568 nm; Em: >648 nm, for Compound 5) lasers.

Example 4

Detection of Cytosolic Zinc Ions in Mitochondria

Figure 3:
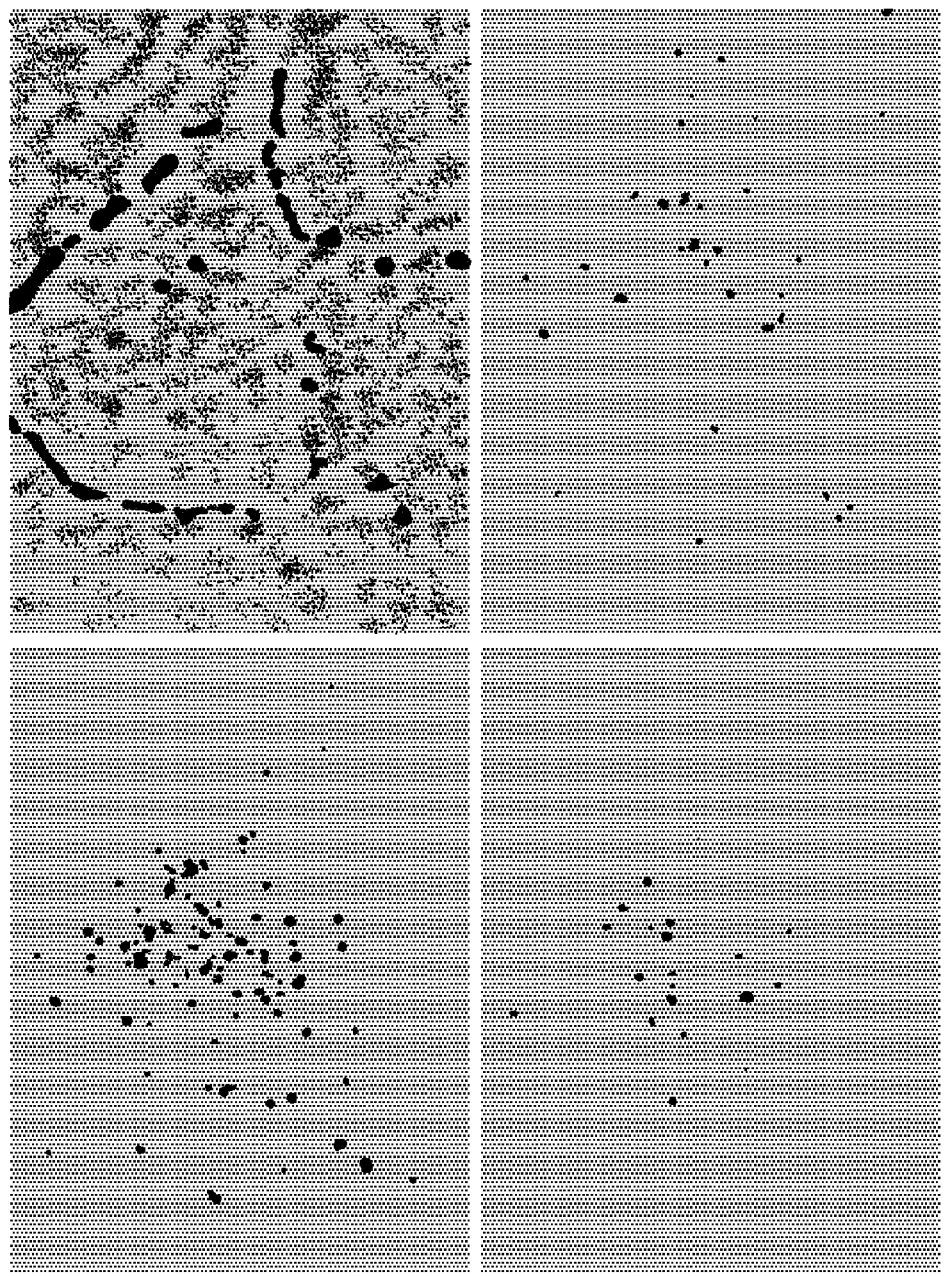
FIG. 3: Shows that Compound 5 detects changes in $[Zn^{2+}]_m$. Neurons loaded with Compound 5 were exposed for 5 min to 50 μM $Zn^{2+}$ in the presence of a depolarizing buffer (high $K^+$). Clockwise from upper left: bright field, basal Compound 5 fluorescence, Compound 5 fluorescence changes after exposure to 50 μM $Zn^{2+}$ and high $K^+$, and finally to the cell permeable $Zn^{2+}$ chelator TPEN (20 μM). Note the substantial increase in Compound 5 fluorescence, that has been converted to Compound 4, upon cytosolic $Zn^{2+}$ loading and it's quenching by the addition of TPEN.

Compound 5 was tested to determine if the compound could effectively detect changes in $[Zn^{2+}]_m$. Cortical neurons were loaded with the AM ester of Compound 4 (Compound 5) and exposed to 50 µM $Zn^{2+}$ in the presence of a depolarizing buffer (60 mM $K^+$) in order to increase cytosolic $Zn^{2+}$ by allowing entry through the opening of voltage sensitive $Ca^{2+}$ channels. Consistent with prior observations of mitochondrial uptake of cytosolic $Zn^{2+}$ loads (Sensi S L, et al., Eur J Neurosci (2000) 12:3813-8; Sensi S L, et al., Neurobiol Dis (2002) 10:100-108), $Zn^{2+}$ entry into the neurons caused an increase in the mitochondrial signal (44.8±4.3% increase; 177 neurons from 8 experiments). Indicating that the observed changes in the fluorescence of Compound 5, after being converted to Compound 4 in the neurons, were indeed due to $Zn^{2+}$ uptake, punctuate regions of strong fluorescence were attenuated by addition of the $Zn^{2+}$ selective chelator, TPEN (see, FIG. 3).

Example 5

Synthesis of Compound 13

Compound 7 (Grynkiewicz G, Poenie M, Tsien R Y, J. Biol. Chem. 1985, 260: 3440-3450) is dissolved in DMF at 0.5 M and treated with 2 eq of Vilsmeyer reagent prepared from POCl₃ and DMF. After stirring at room temperature until TLC (EtOAc/hexanes 1:1) indicates complete formation of a more polar product, the reaction solution is poured into excess aqueous sodium acetate. The resulting precipitate is collected by filtration, rinsed with water, and dried in vacuo to give compound 8 as a yellow powder.

Compound 8 is dissolved in ethyl acetate at 0.25 M, and treated with 20% wt of 10% platinum on carbon. The resulting mixture is shaken under hydrogen (30 psi) until TLC (10% methanol/chloroform) indicates complete formation of compound 9. The catalyst is filtered off using diatomaceous earth, and the filtrate concentrated in vacuo to give 9 as a pale brown immobile oil.

Compound 9 is dissolved in DMF at 0.25 M, and treated with 3 eq of bromomethyl acetate and 3 eq of diisopropylethylamine (DIEA). The resulting solution is heated to 90° C. for 3 hours, then cooled to room temperature and poured into excess water. The resulting mixture is extracted with ethyl acetate (3×). The extract is washed with water and brine, dried over sodium sulfate, and concentrated in vacuo to give compound 10, which can be further purified by trituration with ether and/or flash chromatography on silica gel using ethyl acetate/hexanes.

Compound 10 is dissolved in 1% acetic acid/dichloromethane at 0.5 M and treated with 10% wt of 10% Pd/C. The resulting mixture is shaken under hydrogen (40 psi) until TLC (ethyl acetate/hexanes) indicates complete conversion to a more polar product. The catalyst is filtered off using diatomaceous earth, and the filtrate concentrated in vacuo to give 11 as a pale brown immobile oil.

Compound 11 is dissolved in DMF (0.1 M) and treated with 1 eq of ethyl 5-chloromethyloxazole-2-carboxylate (Grynkiewicz G, Poenie M, Tsien R Y, J. Biol. Chem. 1985, 260: 3440-3450) and 1.5 eq of potassium carbonate. The resulting mixture is heated at 130° C. for 4 hours. Formation of 12 is indicated on TLC (ethyl acetate/hexanes) by formation of an intensely blue-green fluorescent product. After cooling to room temperature, the reaction mixture is poured into excess water. The resulting mixture is extracted with ethyl acetate (3×). The extract is washed with water and brine, dried over sodium sulfate, and concentrated in vacuo to give compound 12, which can be further purified by trituration with ether and or flash chromatography on silica gel using ethyl acetate/hexanes.

Compound 12 is dissolved in 1:1 methanol/dioxane (0.1 M) and treated with 8 eq of aqueous KOH. The resulting solution is kept at room temperature for 12 hours, then concentrated in vacuo to give compound 13. For further purification, the compound is dissolved in water, and the pH (~13) is lowered to 1 by careful addition of aqueous HCl. The resulting precipitate is collected by filtration on a Buchner funnel, giving compound 13 in free acid form as a yellow powder. The free acid form of 13 can be treated with aqueous KOH to give 13, which can be purified further by chromatography on Sephadex LH-20 using water as eluant; pure product fractions are pooled and lyophilized to give 13 as a fluffy yellow powder.

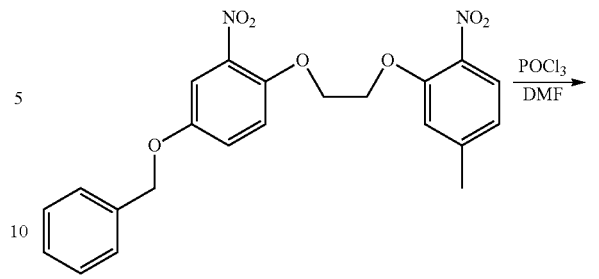

7

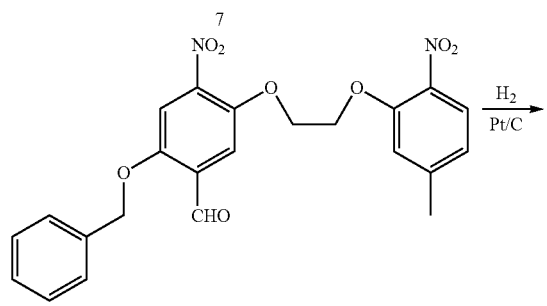

8

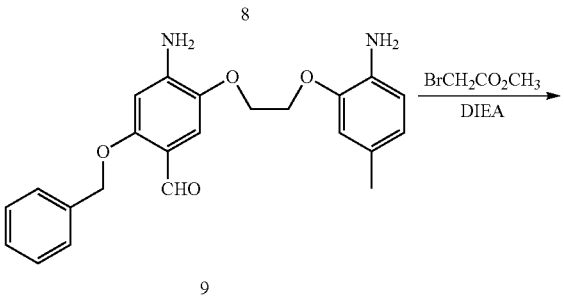

9

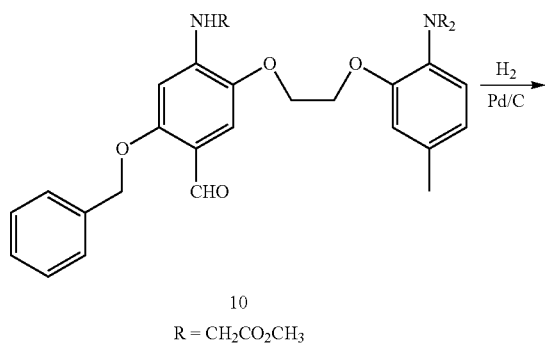

10
R = CH₂CO₂CH₃

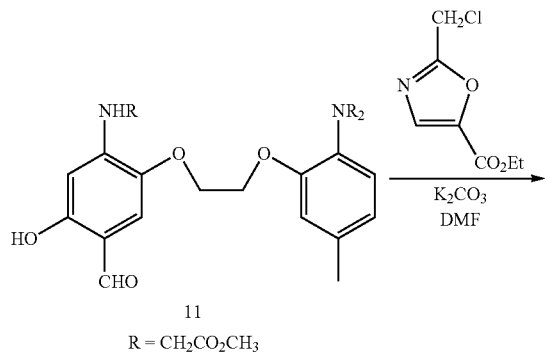

11
R = CH₂CO₂CH₃

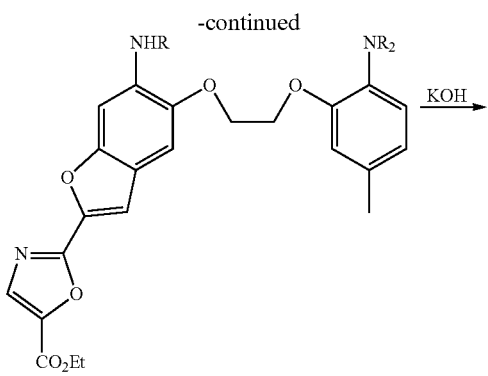

12
R = CH₂CO₂CH₃

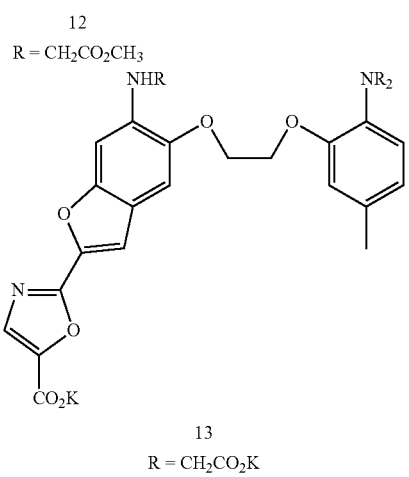

13
R = CH₂CO₂K

Example 6

Detection of Insulin/$Zn^{2+}$ after with Compound 4 after Secretion from Murine Pancreatic β-Cells Pancreatic islets are isolated from CD-1 mice and dispersed into single cells and cell clusters by shaking in dilute trypsin for 10 minutes at 37° C. Islets or dispersed cells are plated onto coverslips in tissue culture dishes and incubated in RPMI 1640 medium containing 10% fetal bovine serum, 100 U/mL penicillin and 100 pg/mL streptomycin at 37° C., 5% $CO_2$, pH 7.4.

Imaging experiments are performed on a laser scanning confocal microscope equipped with a krypton laser (Ex: 568 nm, Em: >648 nm) and 20× to 60× objectives. Kreb's Ringer buffer is prepared with all ingredients except calcium and magnesium salts and the buffer is treated with Chelex-100 (Bio-Rad) for 2 hours (5 g Chelex-100 per 100 mL buffer). The pH of the buffer is adjusted to 7.4 after Chelex-100 treatment and Puratronic grade $CaCl_2$ and $MgCl_2$ (Alfa AESAR) are added to the final concentrations. Cells or islets to be imaged are bathed in buffer containing 2 μM Compound 4 and maintained at 37° C. on the stage of the microscope by a microincubator. If necessary, the buffer is titrated with tetrakis-(2-picolyl)ethylenediamine (TPEN) to deplete the trace amount of $Zn^{2+}$ present in the buffer in order to reduce background fluorescence. The typical final concentration of TPEN in the buffer is ~200 nM. For stimulation, secretagogues are applied to the cells by pressure ejection at 3-6 psi from micropipettes positioned ~60 μm from the cells. Stimulation (30 mM $K^+$ or 20 mM glucose) solutions contain the same concentration of Compound 4 as the bathing buffer. For continuous stimulation with an elevated concentration of glucose, cells are either directly incubated in buffer containing the desired concentration of glucose or incubated in buffer containing 3.0 mM glucose and aliquots of concentrated glucose (1 M) are added to obtain the desired concentration at the time of stimulation.

Upon stimulation, increases in fluorescence are observed in the extracellular space due to the binding of Compound 4 with released insulin/$Zn^{2+}$. Diffusional dilution of released insulin/$Zn^{2+}$ can be observed as the insulin/$Zn^{2+}$ level decreases in areas located progressively farther away from the cells.

Example 7

Preparation of $Zn^{2+}$-Binding Agarose

A 0.5M solution of 1,2-bis(2-aminophenoxy)ethane in DMF is treated with 3 equivalents of methyl bromoacetate and 3 equivalents of DIEA. The resulting solution is heated under argon to 90° C., and the reaction progress is monitored by TLC. After several hours, or after TLC indicates substantial tri-N-alkylation, the reaction mixture is cooled and diluted with brine. The resulting mixture is extracted with ethyl acetate (3×). The extract is washed with water (1×) and brine (1×), dried over sodium sulfate, and concentrated in vacuo. The residue is purified by flash chromatography using ethyl acetate in hexanes to separate the trialkylated product 14 from under- and over-alkylated by-products. Pure product fractions are pooled and concentrated to give 14 as a pale brown solid, which is further purified by crystallization from methanol if needed.

A 0.5M solution of 15 in chloroform is chilled on ice and treated with a 10-fold excess of trifluoroacetic anhydride. The reaction is monitored by TLC for formation of amide 15. Once the reaction is complete, the volatiles are removed in vacuo and toluene (1×) stripped from the residue, which is purified by crystallization from methanol to give pure 15.

A 0.1 M solution of 14 in acetic anhydride is chilled on ice and treated dropwise with 1.0 equivalents of nitric acid (70%). The reaction mixture is stirred on ice and monitored by TLC. Once consumption of 15 is apparent, the reaction mixture is poured into excess water. The resulting precipitate is collected by suction filtration, rinsed with water, and dried in vacuo to give a yellow solid. This solid is purified by flash chromatography using ethyl acetate in chloroform or crystallization from methanol to give pure 16.

A 0.1 M solution of 16 in 1:1 methanol/dioxane is treated with 10 equivalents of 1M aqueous KOH. The resulting solution is stirred overnight at rt, then concentrated in vacuo. The residue is dissolved in water to 0.1 M, and the pH is lowered carefully to 2.0 by dropwise addition of dilute HCl. The resulting precipitate is collected by suction filtration, rinsed with water, and dried in vacuo to give compound 17.

A 0.1 M solution of 17 in methanol is shaken with 10 wt % of 10% Pd/C under 40 psi hydrogen gas for 6 hours, then filtered through diatomaceous earth and concentrated in vacuo to give compound 18.

A 0.05M solution of 18 in water containing one drop of conc. HCl is treated with an equal volume of chloroform. The resulting biphasic mixture is treated with 50 equivalents of thiophosgene, and the resulting mixture stirred vigorously overnight. The organic volatiles are removed by rotary evaporation, and the resulting aqueous mixture is centrifuged. The supernatant is discarded and the residual solids rinsed with excess water, then dried in vacuo to give compound 19. Further purification can be effected by slow addition of a concentrated solution of 19 in THF to hexanes with stirring. The resulting precipitate is collected by suction filtration and dried in vacuo.

A 0.05M solution of compound 19 in DMF is added to a 50% aqueous slurry of aminoagarose (Pierce 20266, containing an equimolar amount of amine groups) that has been diluted 3-fold with DMF. DIEA is added to raise the reaction pH to 8-9. The resulting slurry is shaken or stirred overnight at rt, then centrifuged. The solids are rinsed with acetone (2×) and water (2×), then resuspended in water to give an aqueous slurry of zinc-binding agarose, compound 20.

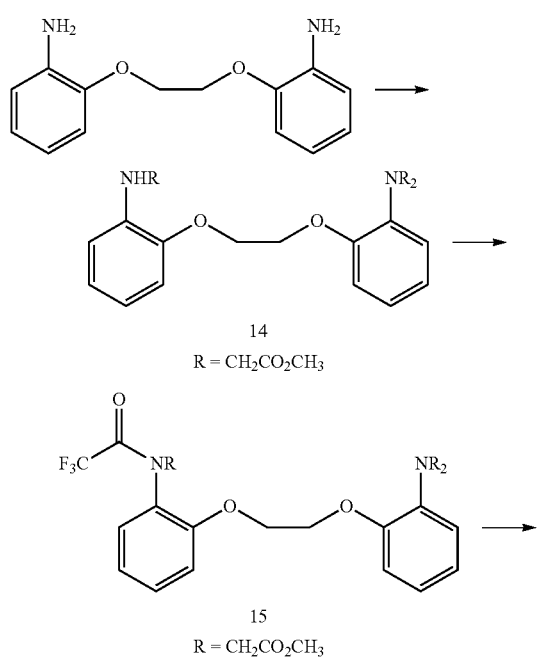

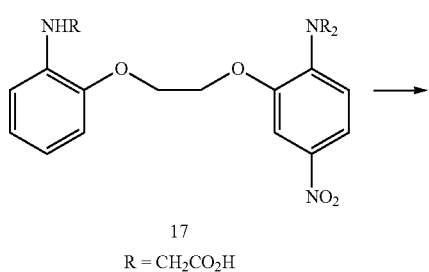

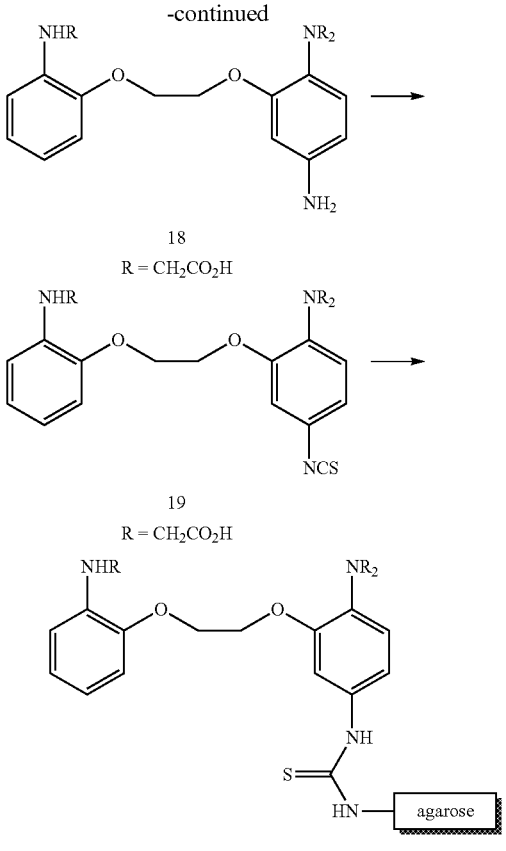

Example 8

N,N-Diacetic Zinc-Binding Compounds

From the purification by water chromatography on Sephadex LH-20 of the reaction mixture obtained by saponification of compound 3, a small amount of a less polar material is separated from 4. LCMS characterization of this less polar material indicates it to be the N,N-diacetic derivative of 4, i.e. compound 21 or 22. Spectroscopic analysis indicates the compound 21 (or 22) to be non-fluorescent until it binds $Zn^{2+}$, and that its affinity for $Zn^{2+}$ is lower compared to 4.

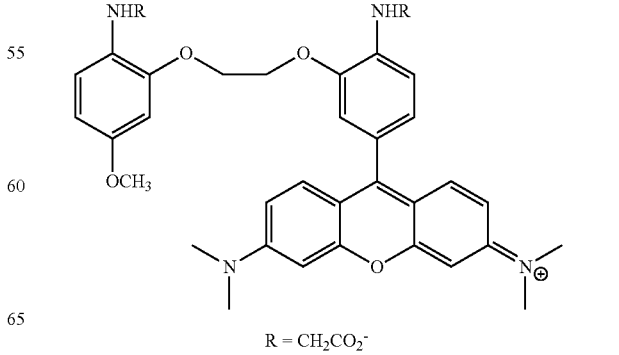

-continued

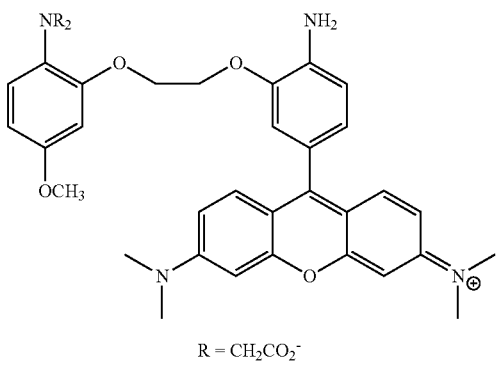

22

R = CH₂CO₂⁻

The preceding examples can be repeated with similar success by substituting the specifically described zinc-binding compounds and zinc binding conditions of the preceding examples with those generically and specifically described in the forgoing description. One skilled in the art can easily ascertain the essential characteristics of the present invention, and without departing from the spirit and scope thereof, can make various changes and modifications of the invention to adapt to various usages and conditions.

Recent years have seen a rapid increase in our understanding of the complex neurobiological effects of $Zn^{2+}$. A better understanding of the intracellular systems controlling $[Zn^{2+}]_i$ homeostasis, and in particular on the role played by mitochondria in such processes is needed. The present invention demonstrates that the present zinc-binding compounds are valuable tools for detecting physiologically and pathophysiologically relevant changes in $[Zn^{2+}]_m$.

All publications, patents and patent applications mentioned in this specification are herein incorporated by reference to the same extent as if each individual publication, patent or patent application was specifically and individually indicated to be incorporated by reference.

What is claimed is:

1. A compound having the formula:

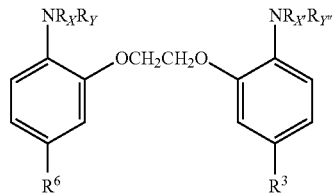

wherein $R_X$ is H, $R_Y$ is $CH_2CO_2R$, $R_{X'}$ is $CH_2CO_2R$ and $R_{Y''}$ is $CH_2CO_2R$, wherein R is H or $CH_2OC(O)CH_3$;
wherein $R^3$ is methoxy (—$OCH_3$); and
wherein $R^6$ is a reporter molecule, the reporter molecule is a 3-aminoxanthene-6-imine.

2. The compound according to claim 1, wherein said R is H.

3. The compound according to claim 1, wherein said R is $CH_2OC(O)CH_3$.

4. The compound according to claim 1, wherein said compound is

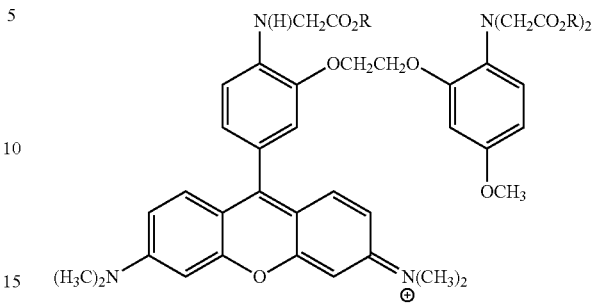

and a biologically compatible anion.

5. The compound according to claim 1, wherein said compound is

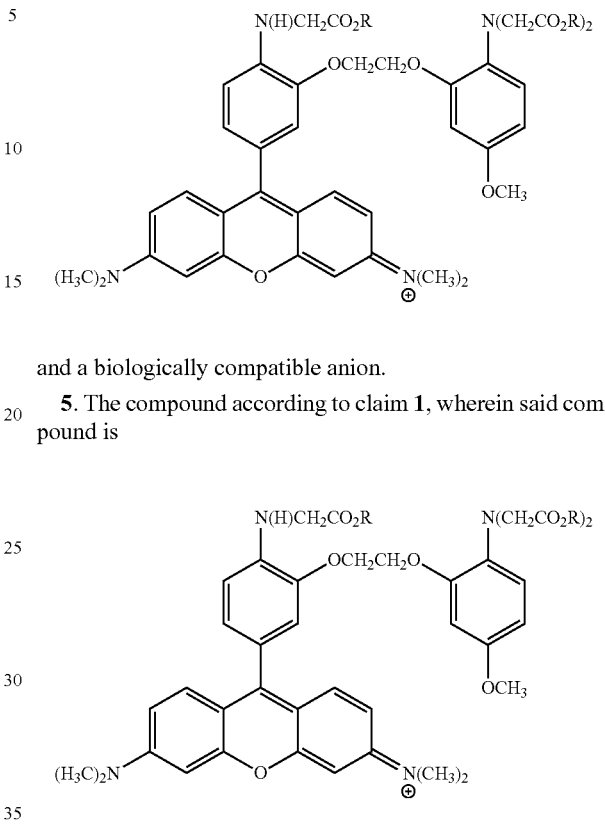

with a biologically compatible anion, wherein R is $CH_2OC(O)CH_3$.

6. A kit comprising at least one compound according to the formula:

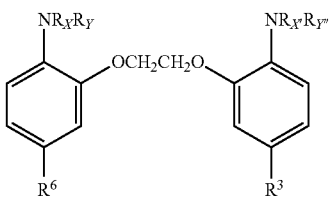

wherein $R_X$ is H, $R_Y$ is $CH_2CO_2R$, $R_{X'}$ is $CH_2CO_2R$ and $R_{Y''}$ is $CH_2CO_2R$, wherein R is H or $CH_2OC(O)CH_3$;
wherein $R^3$ is methoxy (—$OCH_3$); and
$R^6$ is a reporter molecule, the reporter molecule is a 3-aminoxanthese-6-imine.

7. The kit according to claim 6, wherein said kit independently further comprises; a buffer, an additional detection reagent, a metal ion calibration reagent, a positive control, a metal ion indicator other than for zinc ions, an antibody or fragment thereof or a reference dye standard.

8. The kit according to claim 6, wherein said R is H.

9. The kit according to claim 6, wherein said R is $CH_2OC(O)CH_3$.

10. The kit according to claim 6, wherein said compound is
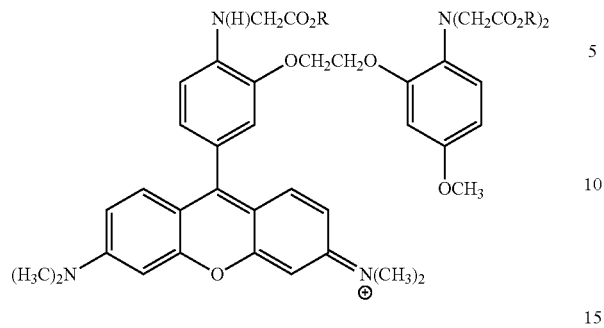
and a biologically compatible anion.
* * * * *

UNITED STATES PATENT AND TRADEMARK OFFICE
CERTIFICATE OF CORRECTION

| | | |
|---|---|---|
| PATENT NO. | : 8,445,702 B2 | Page 1 of 1 |
| APPLICATION NO. | : 13/030743 | |
| DATED | : May 21, 2013 | |
| INVENTOR(S) | : Kyle Gee | |

It is certified that error appears in the above-identified patent and that said Letters Patent is hereby corrected as shown below:

On the Title Page of the Issued Patent, item (75) Inventors, please correct the following city:
"Springfiled" to --Springfield--.

On the Title Page of the Issued Patent, item (63) Related U.S. Application Data, please correct the following:
"filed on May 5, 2004, now abandoned." to --filed on May 5, 2004, now abandoned, claiming the benefit of U.S. provisional 60/468,173, filed May 5, 2003, now expired.--.

Signed and Sealed this
Twenty-eighth Day of January, 2014

Michelle K. Lee
*Deputy Director of the United States Patent and Trademark Office*